(12) United States Patent
Jordan et al.

(10) Patent No.: US 6,582,226 B2
(45) Date of Patent: *Jun. 24, 2003

(54) ORTHODONTIC APPLIANCE WITH SELF-RELEASING LATCH

(75) Inventors: Russell A. Jordan, Rancho Cucamonga, CA (US); Ming-Lai Lai, Arcadia, CA (US); Evangelos G. Georgakis, Alta Loma, CA (US); Robert C. Manemann, Corona, CA (US); Oscar M. Binder, Anaheim Hills, CA (US); James D. Cleary, Glendora, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/848,030

(22) Filed: May 3, 2001

(65) Prior Publication Data

US 2001/0029008 A1 Oct. 11, 2001

Related U.S. Application Data

(63) Continuation-in-part of application No. 09/405,751, filed on Sep. 27, 1999, now Pat. No. 6,302,688.

(51) Int. Cl.[7] .................................................. A61C 3/00
(52) U.S. Cl. ...................................................... 433/10
(58) Field of Search ............................. 433/8, 9, 10, 11

(56) References Cited

U.S. PATENT DOCUMENTS

| | | | |
|---|---|---|---|
| 1,991,047 A | 2/1935 | Boyd et al. | |
| 3,052,027 A | 9/1962 | Wallshein | |
| 3,084,437 A | 4/1963 | Neger | |
| 3,327,393 A | 6/1967 | Brader | |
| 3,464,112 A | * 9/1969 | Silverman et al. | 433/11 |
| 3,464,113 A | * 9/1969 | Silverman et al. | 433/11 |
| 3,724,074 A | 4/1973 | Wallshein | |
| 3,772,787 A | 11/1973 | Hanson | |
| 4,103,423 A | 8/1978 | Kessel | |
| 4,149,314 A | 4/1979 | Nonnenmann | |
| 4,171,568 A | 10/1979 | Forster | |
| 4,197,642 A | 4/1980 | Wallshein | |
| 4,248,588 A | 2/1981 | Hanson | |
| 4,260,375 A | 4/1981 | Wallshein | |
| 4,492,573 A | 1/1985 | Hanson | |
| 4,496,318 A | 1/1985 | Connelly, Jr. | |
| 4,551,094 A | 11/1985 | Kesling | |
| 4,559,012 A | 12/1985 | Pletcher | |
| 4,698,017 A | 10/1987 | Hanson | |
| 4,712,999 A | 12/1987 | Rosenberg | |
| 4,725,229 A | 2/1988 | Miller | |
| 4,846,681 A | 7/1989 | Mourany et al. | |

(List continued on next page.)

FOREIGN PATENT DOCUMENTS

WO    WO98/20805    5/1998

OTHER PUBLICATIONS

Voudouris, John C. "Seven Clinical Principles of Interactive Twin Mechanisms", *Journal Clinical Orthodontics, Inc.* 1997, vol. XXXI, No. 1, pp. 55–65.

*Primary Examiner*—Todd E. Manahan
(74) *Attorney, Agent, or Firm*—James D. Christoff

(57) ABSTRACT

An orthodontic appliance such as a bracket or buccal tube has a latch for retaining an archwire in an archwire slot. The latch releases the archwire from the archwire slot whenever the archwire exerts a force on the appliance that exceeds a certain minimum value. The minimum value is less than about one-half of the force required in the same direction to debond the appliance from the tooth, and thus reduces the likelihood that the appliance will unintentionally debond from the tooth during the course of orthodontic treatment.

52 Claims, 21 Drawing Sheets

U.S. PATENT DOCUMENTS

| | | |
|---|---|---|
| 5,039,302 A | 8/1991 | Keys |
| 5,269,681 A | 12/1993 | Degnan |
| 5,322,435 A | 6/1994 | Pletcher |
| 5,356,289 A | 10/1994 | Watanabe |
| 5,466,151 A | 11/1995 | Damon |
| 5,474,445 A | 12/1995 | Voudouris |
| 5,516,284 A | 5/1996 | Wildman |
| 5,562,444 A | 10/1996 | Heiser et al. |
| 5,630,715 A | 5/1997 | Voudouris |
| 5,630,716 A | 5/1997 | Hanson |
| 5,685,711 A | 11/1997 | Hanson |
| 5,711,666 A | 1/1998 | Hanson |
| 5,857,849 A | 1/1999 | Kurz |
| 5,857,850 A | 1/1999 | Voudouris |
| 5,863,199 A | 1/1999 | Wildman |
| 5,890,893 A | 4/1999 | Heiser |
| 5,908,293 A | 6/1999 | Voudouris |
| 5,913,680 A | 6/1999 | Voudouris |
| 5,967,773 A | 10/1999 | Roman et al. |
| 5,971,753 A | 10/1999 | Heiser |
| 6,168,428 B1 | 1/2001 | Voudouris |

\* cited by examiner

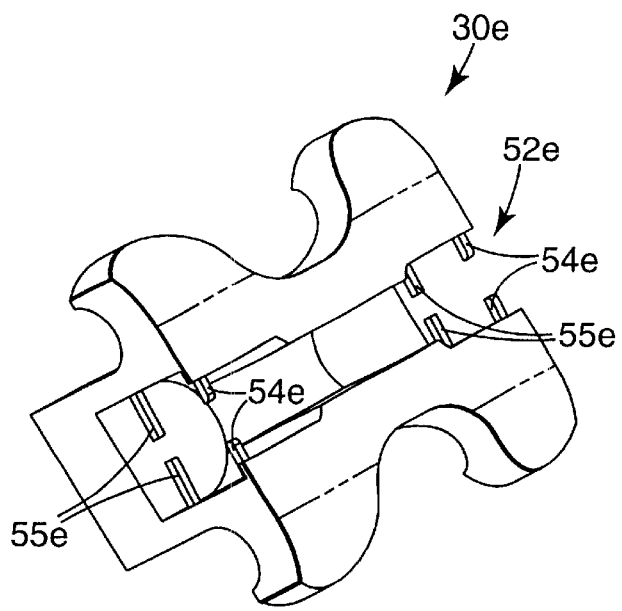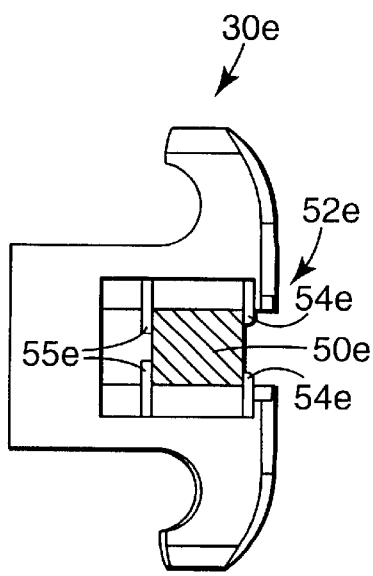
Fig. 10          Fig. 11
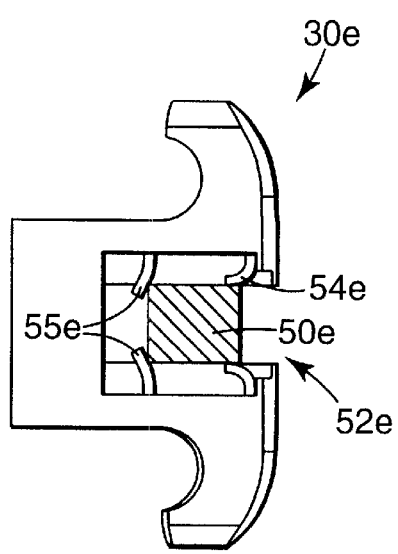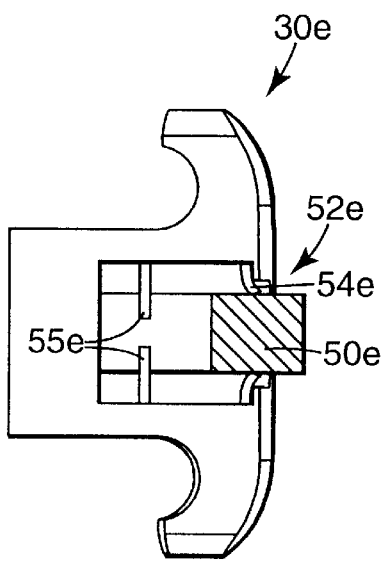
Fig. 12          Fig. 13

ORTHODONTIC APPLIANCE WITH SELF-RELEASING LATCH

This is a continuation-in-part of application Ser. No. 09/405,751 filed Sep. 27, 1999 now U.S. Pat. No. 6,302,688.

BACKGROUND OF THE INVENTION

1. Field of the Invention

This invention broadly relates to an appliance used in orthodontic treatment. More particularly, the present invention relates to an orthodontic appliance such as a bracket or buccal tube having a releasable latch for releasably retaining an archwire in an archwire slot of the appliance.

2. Description of the Related Art

Orthodontic therapy is a specialized type of treatment within the field of dentistry, and involves movement of malpositioned teeth to orthodontically correct locations. Orthodontic treatment often improves the patient's occlusion and typically enhances the aesthetic appearance of the teeth.

Many types of orthodontic treatment programs involve the use of a set of tiny appliances and wires that are commonly known collectively as "braces". During such treatment programs, small appliances known as brackets are fixed to the patient's anterior, cuspid and bicuspid teeth, and an archwire is inserted into a slot of each bracket. The archwire forms a track to guide movement of the teeth to orthodontically correct locations. End sections of the archwires are typically captured in tiny appliances known as buccal tubes that are fixed to the patient's molar teeth.

Many types of orthodontic brackets have archwire slots that are open on one side for insertion of the archwire, and bounded on remaining sides by walls or other structure. Brackets that are intended to be bonded to the patient's front tooth surfaces often have archwire slots that are open either on a buccolabial side (i.e., a side facing the patient's cheeks or lips) or an occlusal side (i.e., a side facing the outer tips of the teeth) of the archwire slot. Some brackets, however, are intended to be fixed to the lingual side of the patient's teeth (i.e., the side of the teeth facing the patient's tongue) and in that instance typically have an archwire slot that is open on a lingual side or on an occlusal side.

Many orthodontists use ligatures to connect the archwire to the brackets and to urge the archwire into an orientation of seating engagement in the archwire slot. One type of commercially available orthodontic ligature is a small, elastomeric O-ring. Orthodontic O-rings are installed by stretching the O-ring around small wings (known as "tiewings") that are connected to the bracket body on the gingival side (i.e., the side facing the patient's gingiva or gums) and on the occlusal side of the archwire slot. Once installed, the O-ring ligature extends around the tiewings as well as over the labial side of the archwire and urges the archwire toward a fully seated position in contact with a lingual wall of the archwire slot.

Metal ligatures, such as ligatures made of stainless steel, are also used to retain archwires in archwire slots of brackets. Metal ligatures are typically made of a short section of initially straight wire. During installation, the wire ligature is hooked around the tiewings and extended over the labial side of the archwire. End sections of the ligature are then twisted together to form a loop to retain the ligature in place.

Unfortunately, some orthodontists are not entirely satisfied with elastomeric and metal ligatures. Such ligatures are somewhat time-consuming to install, both during initial installation and also during reinstallation whenever replacement of the archwire or ligatures is desired. As can be appreciated, a savings in the amount of time needed for ligation can help to reduce the total time that the practitioner must spend with the patient and consequently aid in reducing the overall costs of orthodontic treatment.

Other disadvantages are also associated with elastomeric and metal ligatures. For example, there have been reports that certain polyurethane elastomeric ligatures have exhibited deformation and force decay during the course of treatment. In some instances, elastomeric ligatures are stained by food and beverages consumed by the patient and become somewhat unsightly. Metal ligatures often have sharp ends that may retain plaque and food debris and also may increase the risk of infection.

In an effort to overcome the problems associated with conventional ligatures, a variety of orthodontic brackets have been proposed having various types of latches for coupling the archwire to the bracket. Such brackets are also known as self-ligating brackets. The latch comprises a clip, spring member, cover, shutter, bail or other structure that is connected to the bracket body for retaining an archwire in the archwire slot.

Examples of self-ligating orthodontic brackets having generally U-shaped ligating latch clips are described in U.S. Pat. Nos. 3,772,787, 4,248,588 and 4,492,573. In general, the clip of such brackets is slidably mounted on the bracket body, and a dental explorer or other small-tipped dental tool is used to move the clip relative to the body when needed in order to open or close the archwire slot. A self-ligating bracket known as the "Speed" brand bracket also has a movable, generally U-shaped clip for ligating the archwire to the bracket.

Other types of self-ligating brackets have latches that resemble swinging shutters or closures that pivotally move between a slot-open and a slot-closed position. For example, U.S. Pat. No. 4,712,999 has a rotatable cover plate that is pivotally connected at one end to a tiewing of the bracket along one side of the slot, and is releasably engagable at the other end with a tiewing that is located along the opposite side of the archwire slot. Other orthodontic brackets with swinging latches are described in U.S. Pat. Nos. 4,103,423, 5,516,284 and 5,685,711.

U.S. Pat. Nos. 4,371,337 and 4,559,012 describe self-ligating orthodontic brackets having latches that rotate about the longitudinal axis of the archwire slot. The latch of these references has a somewhat cylindrical shape and is rotatably received in a mating, cylindrical channel, and an outwardly extending arm is provided to assist in rotatably moving the latch between a slot-open and a slot-closed position.

A self-ligating orthodontic bracket that is described in U.S. Pat. No. 5,711,666 has a latch that comprises a flexible flat spring member. One end of the spring member is fixed to the bracket body on one side of the archwire slot, and the opposite end of the spring member has notches that releasably engage latch sears or catches when the spring member is moved to a slot-closed position. To open the slot, the notches are disengaged from the catches and the spring member is bent to an orientation sufficient to enable the archwire to be removed from the archwire slot.

Other types of self-ligating orthodontic brackets have latches that comprise essentially flat plates that are slidable between a slot-open and a slot-closed position. Examples of such construction are shown in U.S. Pat. Nos. 5,094,614, 5,322,435 and 5,613,850. In general, the sliding latches described in those references move in upright channels that are located buccolabially of the archwire slot.

Another type of self-ligating bracket that has been proposed in the past has a latch that is made of a section of wire material that functions similar to a bail. The orthodontic brackets described in U.S. Pat. Nos. 4,149,314, 4,725,229 and 5,269,681 have wire-like latches that swing between a slot-closed position and a slot-open position. The orthodontic bracket described in U.S. Pat. No. 4,260,375 has a wire latch that is slidable between a slot-open and a slot-closed position.

Many practitioners prefer self-ligating orthodontic brackets over brackets that are not self-ligating because the need to ligate each bracket with an initially separate elastomeric O-ring or a metal ligature wire can be avoided. However, conventional self-ligating orthodontic brackets are not entirely satisfactory because of the lack of optimal control over movement of the underlying teeth. During the course of treatment, it may be necessary to shift each tooth relative to adjacent teeth in order to provide an aesthetically pleasing result at the conclusion of treatment. Precise control over movement of the teeth is desirable so that each tooth can be shifted as needed to its exact, intended orientation and in proper orthodontic relation relative to other teeth in the oral cavity.

In general, there are three types of tooth movement that are important to orthodontic practitioners. Tipping movement is one such type of movement, and may be defined as pivotal movement of the long axis of a tooth in a mesial-distal direction. Another movement is torque movement, and can be defined as pivotal movement of the long axis of a tooth in a buccal-lingual direction. The third type of tooth movement is rotational movement, and can be defined as rotational movement of a tooth about its long axis. Preferably, the appliances selected by the practitioner for use provide precise control over movement of the associated teeth for each type of tooth movement.

One problem that has been noted in connection with conventional direct-bonded appliances, including self-ligating brackets, is the possibility that such brackets may spontaneously debond from the patient's tooth when the teeth are severely maloccluded. For example, if one of the patient's teeth is located a relatively large distance in a lingual direction relative to adjacent teeth in the dental arch, the archwire must be deformed a significant distance in order to engage the archwire slot of the bracket. In such instances, the inherent tendency of the archwire to return to its normally arch-shaped configuration will cause the archwire to exert a substantial force on the appliance bonded to the severely maloccluded tooth. Unfortunately, the bracket may then debond from the tooth if the archwire exerts a force that is larger than the force required to debond the bracket in the same direction.

Brackets that spontaneously debond from teeth represent a waste of time and expense for both the practitioner and the patient, and are best avoided if at all possible. Once a bracket has unintentionally debonded from a tooth, the archwire is removed from the slot of each bracket and the tooth is cleaned and etched in preparation to receive another bracket. If the debonding occurs outside of the practitioner's office, the orthodontic treatment of that tooth is interrupted until such time as the patient returns to the practitioner's office for replacement of the bracket.

In the past, practitioners have sometimes used relatively small-diameter archwires in the initial stages of orthodontic treatment when one or more teeth in the dental arch are severely maloccluded. Such archwires provide relatively little force to the appliances, and as a consequence reduce the likelihood that appliances that are directly bonded to severely maloccluded teeth will spontaneously debond during the course of treatment. Unfortunately, the use of such small-diameter archwires somewhat retards the progress of treatment in comparison to the use of larger diameter archwires, since the force provided by the archwire to all of the teeth is somewhat reduced.

While many types of self-ligating orthodontic appliances have been proposed in the past, there remains a continuing need to improve the state of the art so that the treatment program can be completed in prompt fashion, the duration of the patient's appointments can be shortened and the practitioner's efficiency is increased. For example, it would be desirable to provide a self-ligating appliance that reduces the time needed for installation of an archwire in comparison to conventional self-ligating brackets, so that the time of both the practitioner as well as the patient to complete the installation procedure can be reduced. Moreover, it would be desirable if such an appliance could provide precise control over movement of the associated tooth while also facilitating movement of the tooth to its desired ultimate location.

SUMMARY OF THE INVENTION

The present invention is directed toward an orthodontic appliance such as a bracket or buccal tube having features that represent significant advantages over known self-ligating appliances. In one aspect of the invention, the appliance has a latch for releasably retaining an archwire in the archwire slot. The latch releases the archwire from the archwire slot whenever the archwire exerts a force on the appliance that exceeds a certain minimum value. The minimum value is significantly less than the force required in the same direction to debond the appliance from the tooth, and consequently helps ensure that the appliance will not spontaneously debond from the tooth during the course of treatment.

The self-releasing latch of the present invention is also beneficial in that the maximum force exerted by the appliance on the patient's tooth can be limited to a pre-selected value, which in some instances may be lower than the force required to debond the appliance from the tooth. As a result, the amount of any pain experienced by the patient due to forces exerted by the appliance is also limited. The force limiting latch also helps ensure that undue force is not exerted on root portions of the associated tooth so that blood vessels adjacent the root portions are not significantly compressed and blood in the vessels continues to freely circulate to facilitate bone regeneration.

Another aspect of the invention is directed toward a self-ligating appliance having a latch that is movable to a slot-open position to enable passage of an archwire into the slot by pressing the archwire against the latch in a lingual direction. The occlusal side and the gingival side of the archwire slot are immovable relative to each other, and thereby provide good control over movement of the appliance and the associated tooth whenever torquing, tipping, intruding or extruding of the tooth is desired.

Other aspects of the invention relate to a self-ligating orthodontic appliance having a latch that comprises at least one clip. The clip provides certain advantages when manufacturing the appliance, and also enhances the practitioner's control over movement of the associated teeth.

In more detail, the present invention is directed in one embodiment toward an orthodontic appliance that comprises a base for bonding an appliance to a tooth, and a body extending from the base. An archwire slot extends across the body in a generally mesial-distal direction. A latch is connected to the body for releasably retaining an archwire in the archwire slot. The latch releases the archwire from the archwire slot in a certain direction whenever the archwire exerts a force in the range of about 0.1 kg to about 5 kg in the same direction on the appliance.

The present invention is directed in another embodiment toward an orthodontic appliance that comprises a base for bonding the appliance to a tooth and a body extending from the base. The appliance also includes an archwire slot that extends across the body in a generally mesial-distal direction. A latch is connected to the body for releasably retaining an archwire in the archwire slot. The latch releases the archwire from the archwire slot whenever the archwire exerts a force in a certain direction on the appliance that exceeds a certain minimum value. The minimum value is less than about one-half of the force required in the same direction to debond the appliance from the tooth.

Another embodiment of the invention is also directed toward an orthodontic appliance that comprises a base for bonding the appliance to a tooth and a body extending from the base. An archwire slot extends across the body in a generally mesial-distal direction and has an occlusal side, a gingival side and a lingual side. A channel extends in a generally occlusal-gingival direction along a path located lingually of the archwire slot. A latch is connected to the body for releasably retaining an archwire in the archwire slot. The latch is movable to a slot-open position to enable passage of the archwire into the slot by pressing the archwire against the latch in a direction toward the lingual side of the archwire slot. The latch includes a lingual portion that is received in the channel. The latch also includes a pair of arm portions that extend toward each other along a labial side of the archwire slot.

The present invention is also directed toward a method of releasing an archwire from an archwire slot of an orthodontic appliance. The method includes the act of placing at least one leg of a hand instrument along a tooth-facing side of the archwire. The method also includes the act of manipulating the hand instrument in order to urge the archwire in a direction toward a latch of the appliance. The method further includes the act of pressing the archwire against the latch with sufficient force to open the latch and release the archwire from the archwire slot.

These and other aspects of the invention are described in more detail below and are illustrated in the accompanying drawings.

BRIEF DESCRIPTION OF THE DRAWINGS

FIG. 10 is a perspective view of an orthodontic appliance constructed in accordance with yet another embodiment of the invention;

FIG. 11 is an end elevational view of the orthodontic appliance shown in FIG. 10 and looking toward a mesial side of the appliance, and additionally illustrating in cross-section an archwire that is received in an archwire slot of the appliance;

FIG. 12 is a view somewhat similar to FIG. 11 but showing an example of how the appliance appears as the archwire is moved into the archwire slot;

FIG. 13 is a view somewhat similar to FIG. 11 but showing an example of how the archwire appears as the archwire is released from the archwire slot;

FIG. 43b is an exploded perspective view of the appliance shown in FIG. 43a;

DETAILED DESCRIPTION OF THE PREFERRED EMBODIMENTS

Figure 1:
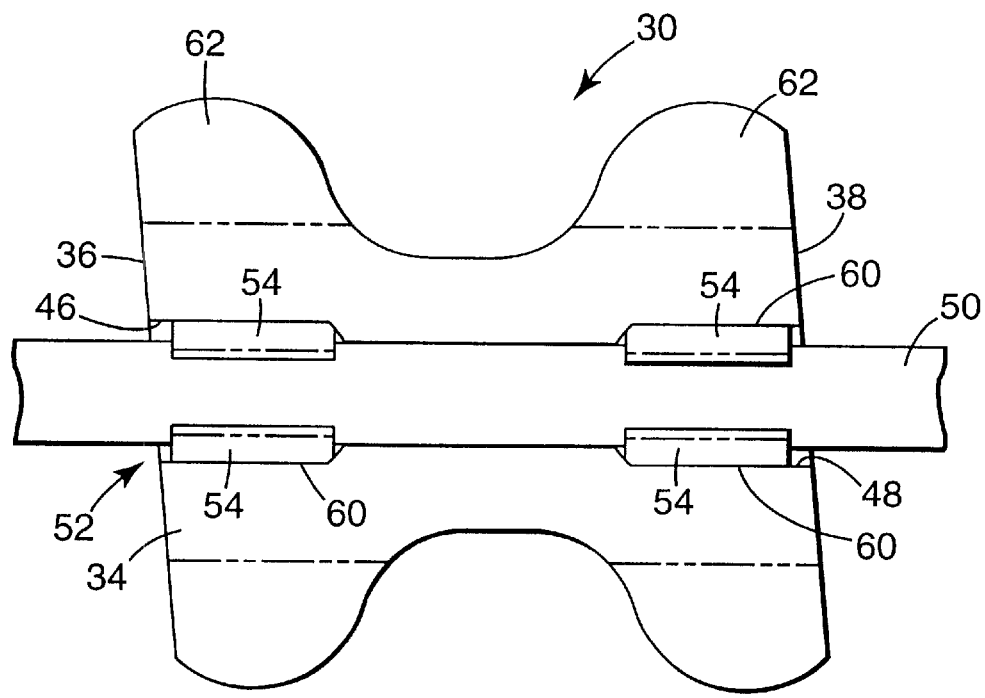
FIG. 1 is a front elevational view looking in a lingual direction toward an orthodontic appliance constructed in accordance with one embodiment of the present invention along with an orthodontic archwire that is received in an archwire slot of the appliance.

An orthodontic appliance constructed in accordance with one embodiment of the present invention is illustrated in FIGS. 1–5 and is broadly designated by the numeral 30. The appliance 30 in this instance is an orthodontic bracket adapted to be secured to the buccolabial surface of a patient's tooth. Alternatively, the appliance could be a buccal tube or any other orthodontic appliance that is adapted to receive an archwire for controlling movement of the teeth during the course of orthodontic therapy.

The appliance 30 includes a base 32 for bonding the appliance 30 directly to the patient's tooth enamel by use of an adhesive. Preferably, the base 32 has a concave compound contour that matches the convex compound contour of the patient's tooth surface. Optionally, the base 32 may be provided with grooves, particles, recesses, undercuts, a chemical bond enhancement material or any other material or structure or any combination of the foregoing that facilitates bonding the appliance 30 directly to the patient's tooth enamel.

A body 34 extends outwardly from the base 32 in a generally buccolabial direction. The body 34 includes an outermost mesial side 36 as well as an outermost distal side 38. In the embodiment shown, the body 34 is integral with the base 32, although in this and in other embodiments other constructions are possible. For example, the base 32 could be comprised of a mesh screen or other bond enhancement structure that is connected by welding, brazing, adhesive or other means to the lingual side of the body 34, and could extend past the body 34 in lateral directions (such as in occlusal-gingival directions).

An archwire slot 40 extends across the body 34 in a generally mesial-distal direction. The archwire slot 40 includes an occlusal side that is defined in part by a flat occlusal wall portion 42 that is fixed to the body 34. The archwire slot 40 also has a gingival side that is defined in part by a flat gingival wall portion 44 that is also fixed to the body 34. Alternatively, the wall portions 42, 44 could be curved, or part of ridges, bumps or other types of protrusions. The wall portions 42, 44 are immovable relative to each other and parallel to each other.

In the embodiment shown in FIGS. 1–5, the appliance 30 includes a mesial archwire slot relief area 46 and a distal archwire slot relief area 48. The relief areas 46, 48 are optional, but advantageously provide greater interbracket width and enhanced control over movement of the tooth as described in U.S. Pat. No. 4,531,911, the disclosure of which is incorporated by reference herein. The parallel wall portions 42, 44 are spaced apart a distance adapted to matingly engage occlusal and gingival sides respectively of an archwire 50 having a certain rectangular, cross-sectional configuration, so that precise control is afforded over tipping and torquing movement of the associated tooth.

The appliance 30 also includes a latch 52 that is connected to the body 34 for releasably retaining the archwire 50 in the archwire slot 40. In this embodiment, the latch 52 includes two pair of arm portions 54 as well as a spring member 56. The arm portions 54 are flat and connected to the body 34 in locations adjacent the archwire slot relief areas 46, 48, although other locations are also possible.

The arm portions 54 are resilient and can be deformed in either a lingual direction or a buccolabial direction. Suitable materials for the arm portions 54 include flat spring material made, for example, of stainless steel or of a shape memory alloy (such as nitinol). The arm portions 54 may be fixed to the body 34 by any suitable technique such as brazing or welding (including laser welding) or by use of fasteners or the like.

The spring member 56 extends along the length of the archwire slot 40 and is optionally made from an intially flat section of metallic material that is bent to an appropriate shape. In the embodiment shown in the drawings, the spring member 56 has a middle portion that is received in a sleeve coupling 58. In turn, the coupling 58 is secured to the body 34 adjacent a central area of the lingual side of the archwire slot 40.

Suitable materials for the spring member 56 include stainless steel alloys as well as shape-memory alloys. If the spring member 56 and the body 34 are both made of stainless steel, the middle portion of the spring member 56 can simply be brazed or welded to the body 34 and the sleeve 58 can be omitted. On the other hand, if the spring member 56 is made of a shape-memory alloy such as nitinol and the body 34 is of stainless steel, it may be difficult to weld or braze the nitinol spring member 56 to the stainless steel body 34. In that instance, the sleeve 58 when made of stainless steel can be readily brazed or welded to the body 34 and will provide a means for securely connecting the spring member 56 to the body 34.

The spring member 56 includes an outermost mesial portion and an outermost distal portion. The mesial and distal portions define the lingual side of the archwire slot 40 and rest against a lingual wall of the archwire 50 when the latter is fully seated in the archwire slot 40. Preferably, the spring member 56 is constructed so that the mesial and distal portions of the spring member 56 engage the lingual side of the archwire 50 and urge the archwire 50 into contact with a lingual surface of the arm portions 54.

Figure 4:
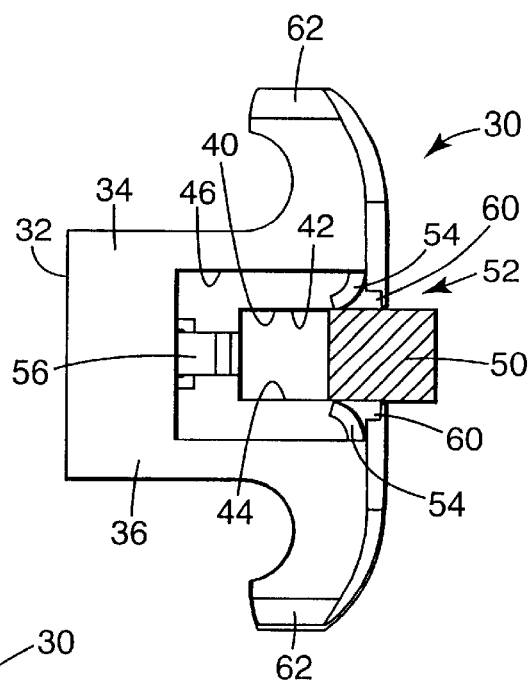
FIG. 4 is a view somewhat similar to FIG. 3 but showing an example of how the latch appears as the archwire is pushed into the archwire slot.

FIG. 4 is an exemplary illustration of how the appliance 30 might appear during the time that the archwire 50 is inserted into the archwire slot 40. As shown, the arm portions 54 deflect inwardly in a generally lingual direction to a degree sufficient to provide clearance and enable passage of the archwire 50 into the archwire slot 40. The arm portions 54 in this embodiment deflect inwardly in an arc about a reference axis that extends parallel to the archwire slot 40, although other constructions are possible.

Advantageously, the arm portions 54 self-deflect inwardly to such a slot-open position as the practitioner presses the archwire 50 against the arm portions 54. As a result, no hand instruments are necessary to move the latch 52 to a slot-open position.

Once the archwire 50 is received in the archwire slot 40a sufficient distance to engage the mesial and distal portions of the spring member 56, continued movement of the archwire 50 in a lingual direction will deform the spring member 56 and enable the mesial and distal portions to be deflected in a lingual direction. Additional movement of the archwire 50 in a lingual direction will then cause the spring member 56 to somewhat flatten and approach a generally planar configuration until such time as the buccolabial side of the archwire 50 has been moved past the outer, facing ends of the arm portions 54.

Figure 2:
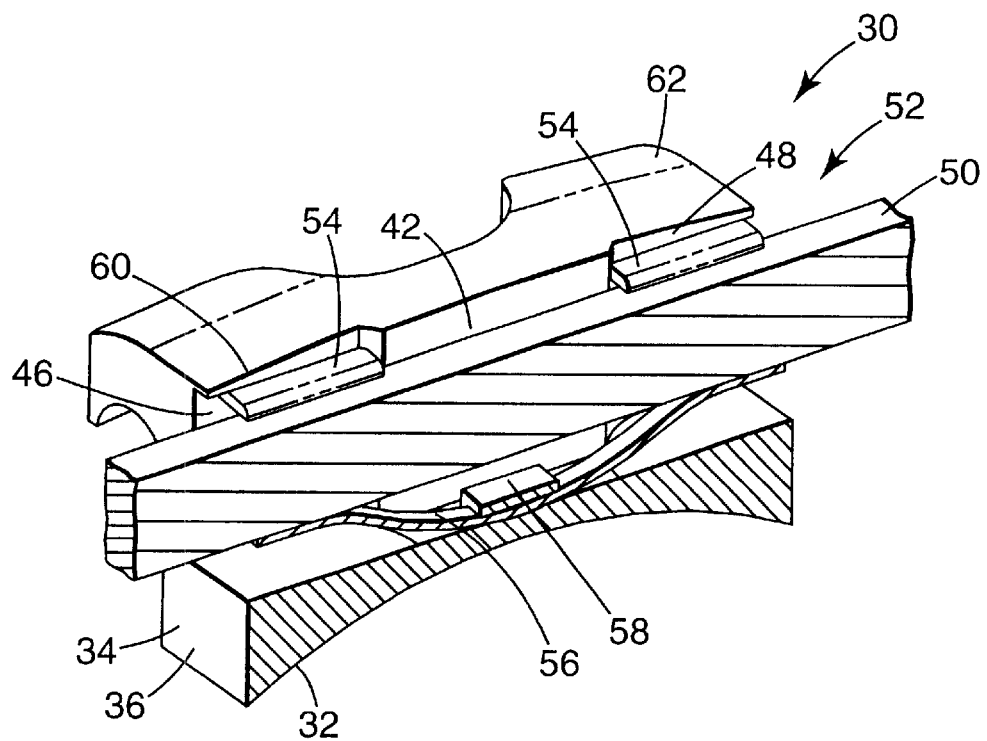
FIG. 2 is a cross-sectional perspective view of the appliance shown in FIG. 1 and illustrating in more detail a latch for releasably retaining the archwire in the archwire slot.
Figure 3:
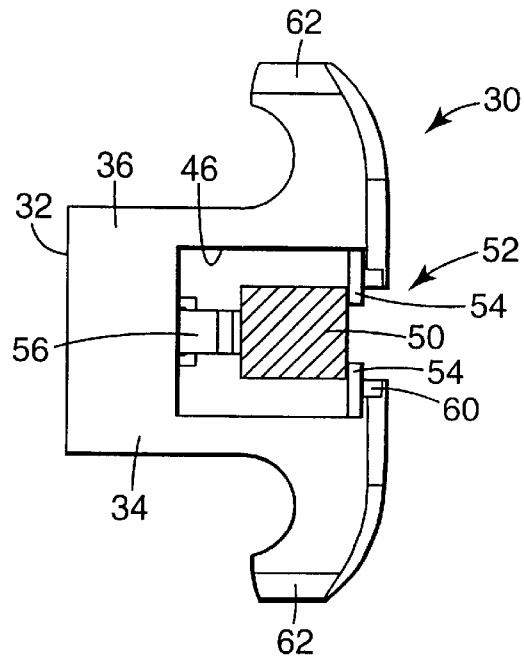
FIG. 3 is an end elevational view looking toward a mesial side of the appliance and the archwire of FIGS. 1 and 2.

Once the buccolabial side of the archwire 50 is clear of the outer ends of the arm portions 54, the arm portions 54 self-deflect in a buccolabial direction and return to their normal shape as shown in FIGS. 1–3. At that time, pressure on the archwire 50 is released by the practitioner and the spring member 56 functions to urge the archwire 50 in a buccolabial direction and toward a position of contact with the lingual side of the arm portions 54. Thereafter, the archwire 50 cooperates with the appliance 30 to provide orthodontic therapy for the associated tooth bonded to the base 32.

Figure 5:
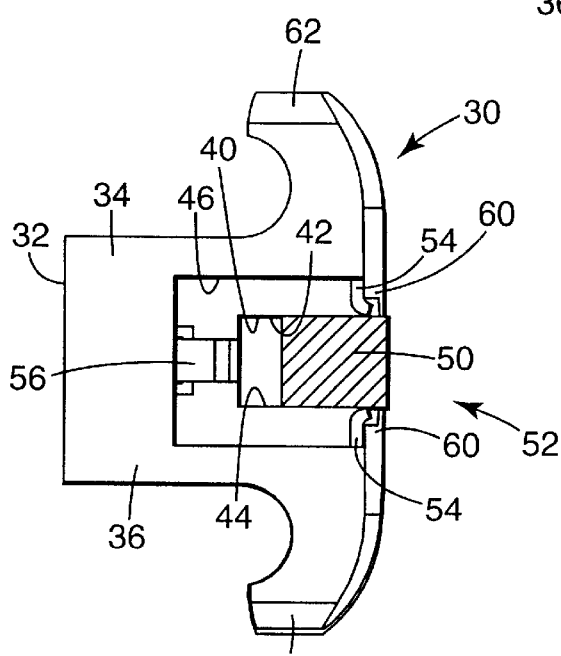
FIG. 5 is a view somewhat similar to FIG. 3 but showing an example of how the latch appears as the archwire is released from the archwire slot.

FIG. 5 is an exemplary illustration of how the appliance 30 might appear during release of the archwire 50 from the archwire slot 40. As shown, the arm portions 54 deflect outwardly to allow movement of the archwire 50 out of the archwire slot 40 in a generally buccolabial direction. The arm portions 54 deflect outwardly by bending in an arc about a reference axis extending parallel to the archwire slot 40, although other constructions are also possible.

Once the archwire 50 has moved in a buccolabial direction a distance sufficient to clear the outer ends of the arm portions 54, the archwire 50 disengages the appliance 30 and the arm portions 54 self-deflect to return to their normally straight, planar orientation as shown in FIGS. 1–3. Preferably, the arm portions 54 as well as the spring member 56 have sufficient resiliency to deflect and deform in the manner described a repeated number of times without exceeding the yield stress of the material of which they are made. As a result, the arm portions 54 and the spring member 56 will consistently return to their original shape and provide predictable results during the entire course of orthodontic therapy even though the latch 52 may open and close numerous times.

Preferably, the buccolabial side of the appliance 30 is provided with four shoulders 60, each of which extends partially over a respective one of the arm portions 54. Optionally, the shoulders 60 are integrally connected to the body 34, although other constructions are also possible. Preferably, the arm portions 54 are not fixed to the shoulders 60 so that the arm portions 54 can move away from the respective shoulders 60 in a lingual direction as the archwire 50 is inserted into the archwire slot 40.

The shoulders 60 provide a resistance to outward deflection (i.e., deflection in a generally buccolabial direction) of the arm portions 54 but provide no resistance to inward deflection (i.e., deflection in a generally lingual direction) of the arm portions 54. The shoulders 60 effectively shorten the length of the arm portions 54 available for outward bending movement, and effectively stiffen the arm portions 54 during outward movement. As a result, a greater force is needed to push the arm portions 54 outwardly and release the archwire 50 from the archwire slot 40 than the force required in the opposite direction to push the arm portions 54 inwardly and enable the archwire 50 to be inserted into the archwire slot 40.

The arm portions 54 deflect outwardly to a slot-open position as shown in FIG. 5 whenever the force exerted by the archwire 50 on the appliance 30 (specifically, in this embodiment whenever the force exerted by the archwire 50 on the arm portions 54) exceeds a certain minimum value. The minimum value is sufficiently high to prevent the archwire 50 from unintentionally releasing from the archwire slot 40 during the normal course of orthodontic treatment. As such, the archwire 50 can exert forces on the appliance 30 sufficient to carry out the treatment program and move the associated tooth as desired. Preferably, the arm portions 54 release the archwire 50 from the archwire slot 40 in a generally buccolabial direction whenever the archwire exerts a force in the same direction on the appliance that is in the range of about 0.2 lb (0.1 kg) to about 11 lb (5 kg), more preferably in the range of about 0.4 lb (0.2 kg) to about 5.5 lb (2.5 kg), and most preferably in the range of about 0.4 lb (0.2 kg) to about 2.7 lb (1.25 kg).

Whenever the force exerted by the archwire 50 on the appliance 30 exceeds the selected minimum value, the arm portions 54 self-deflect outwardly to release the archwire 50 from the archwire slot 40. For example, if the archwire 50 has a relatively large transverse cross-sectional area and is deflected from its normal shape a substantial distance in order to be inserted into the archwire slot 40 (as may occur when the tooth bonded to the appliance 30 is severely maloccluded and located a substantial distance from adjacent teeth), the arm portions 54 will deflect outwardly as soon as the archwire 50 is placed in the archwire slot 40 and pressure by the practitioner in a lingual direction on the archwire 50 is released. As a consequence, the arm portions 54 of the latch 52 substantially preclude the archwire 50 from exerting a force on the appliance 30 that is greater than the minimum value as mentioned above.

To determine the force to release the latch 52, a section of archwire is selected having an area in longitudinally transverse sections that is complemental to (i.e., substantially fills) the cross-sectional area of the archwire slot 40. Next, a sling is constructed and is connected to the archwire section closely adjacent but not in contact with the mesial side 36 and the distal side 38. Optionally, the sling is welded or brazed to the archwire section. Next, the sling is pulled away from the appliance 30 while the appliance 30 is held in a stationary position, taking care to ensure that the longitudinal axis of the archwire section does not tip relative to the longitudinal axis of the archwire slot 40. The force to release the latch 52 is determined by use of an Instron testing apparatus connected to the sling, using a crosshead speed of 0.5 in/min. (1.3 cm/min.).

Preferably, the minimum value for self-release (i.e., self-opening) of the latch 52 is substantially less than the force required in the same direction to debond the appliance 30 from the associated tooth. The minimum value for self-release of the latch 52 is preferably less than about one-half of the force required in the same direction to debond the appliance 30 from the associated tooth. For example, if the expected bond strength of the adhesive bond between the appliance 30 and the associated tooth is 16 lbs. in a buccolabial direction, the latch 52 is constructed to self-release the archwire 50 whenever the archwire 50 exerts a force in the same buccolabial direction on the appliance 30 that is somewhat greater than about 8 lbs. (3.6 kg).

The self-releasing latch 52 is a benefit to the practitioner, in that the likelihood of spontaneous debonding of the appliance 30 is substantially reduced. For example, if the practitioner attempts to place a relatively large archwire in the archwire slot 40 and the latch 52 self-releases as soon as the practitioner releases the archwire, the practitioner can then use an archwire with less stiffness in its place. As another example, if the archwire 50 is initially held in the archwire slot 40 by the arm portions 54 and the archwire 50 subsequently exerts a larger force on the appliance 30 (as may occur, for example, when the archwire 50 encounters a hard object such as when the patient is chewing relatively hard food), the arm portions 54 will deflect outwardly to their slot-open position to release the archwire 50 so that the appliance 30 does not debond from the tooth. Treatment can then be resumed by merely replacing the archwire 50 in the archwire slot 40 without the need to rebond the base 32 to the associated tooth.

Preferably, the distance between the opposed ends of each pair of arm portions 54 is less than the overall occlusal-gingival dimension of the smallest archwire expected to be used during the course of treatment. The archwire 50 need not fill the archwire slot 40 and flatly engage the wall portions 42, 44 in all instances. For example, a somewhat smaller wire, and perhaps a wire having a circular cross-sectional shape, may be used during a portion of the treatment program. The distance between the opposed ends of each pair of spring members 56 is preferably selected so that a variety of archwires of different cross-sectional configurations may be used in connection with the appliance 30.

When an archwire having a relatively large cross-sectional area is placed in the archwire slot 50, the deformable nature of the resilient spring member 56 provides active treatment and facilitates movement of the associated tooth while the appliance 30 moves along the archwire 40. During such movement, the resilient spring member 56 urges the archwire 50 in a direction toward the arm portions 54 and toward a position of flat contact with all four of such arm portions 54. As such, the spring member 56 helps to move the associated tooth to position selected by the practitioner, since the inherent bias of the spring member 56 contributes to the forces exerted on the associated tooth.

Optionally, the appliance 30 includes one or more tiewings or tiewing portions 62. The appliance 30 as illustrated has four tiewings portions 62, each of which is integrally connected to the body 34.

The tiewing portions 62 provide an alternative method of connecting the archwire 50 to the appliance 30. For example, if the archwire 50 cannot be fully inserted into the archwire slot 40 without undue force, the archwire 50 may be ligated to the appliance 30 by passing a ligature around one or more of the tiewing portions 62 as well as around a portion of the archwire 50 without fully seating the archwire 50 in the archwire slot 40. As the associated tooth moves toward a position of alignment with adjacent teeth and closer to the archwire slot 40 over a period of time, less force is needed to fully seat the archwire 50 in the archwire slot 40. At that time, the ligature may then be removed and the archwire 50 retained in the archwire slot 40 by means of the latch 52.

Figure 6:
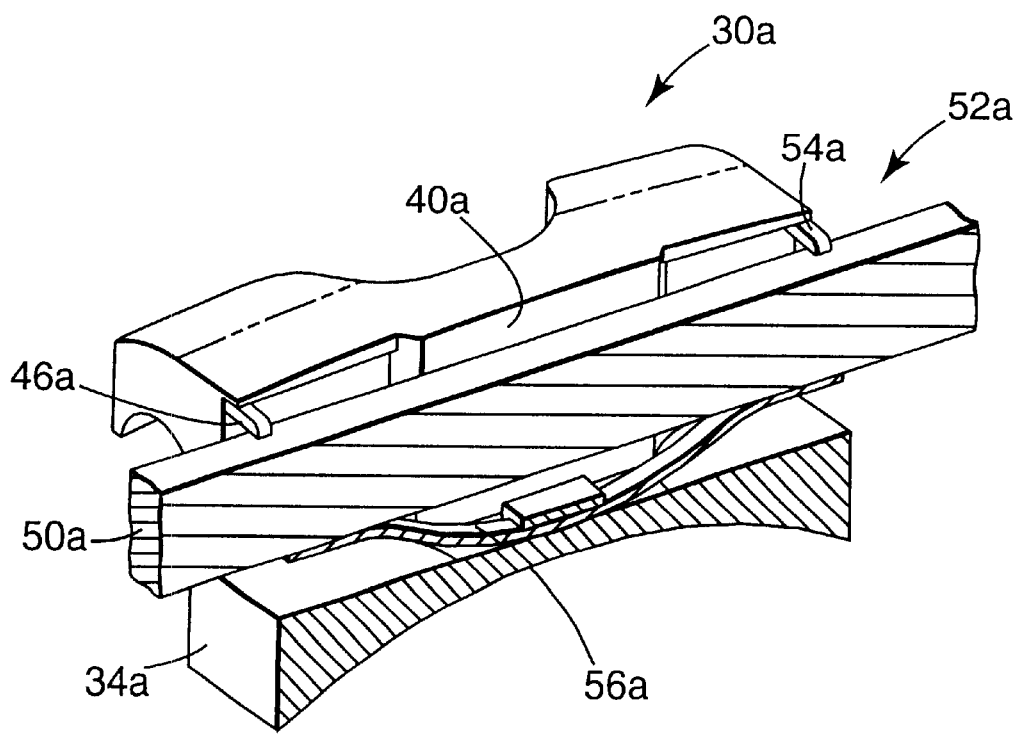
FIG. 6 is a view somewhat similar to FIG. 2 but showing an orthodontic appliance constructed in accordance with another embodiment of the invention.

An orthodontic appliance 30a that is constructed in accordance with another embodiment of the invention is shown in FIG. 6. The appliance 30a is essentially the same as the appliance 30 described above, except for the differences noted below.

The appliance 30a includes a latch 52a having four spaced apart arm portions 54a. The arm portions 54a are somewhat different than the arm portions 54, in that the arm portions 54a are narrower and optionally made of a section of wire material. Optionally, each arm portion 54a may be secured to the body 34a by drilling a small hole in the body 34a to receive a section of the arm portion 54a. The arm portions 54a may be secured in the holes by means of an interference fit, by welding or brazing, by an adhesive, by fasteners or by any other suitable means.

Although only two of the arm portions 54a are illustrated in FIG. 6, the latch 52a has four arm portions 54a that are arranged in opposed pairs in similar fashion to the arrangement of the arm portions 54 of the latch 52. Moreover, the latch 52a has a spring member 56a that is essentially the same as the spring member 56. In all other respects, the appliance 30a is identical to the appliance 30 described above.

Figure 6A:
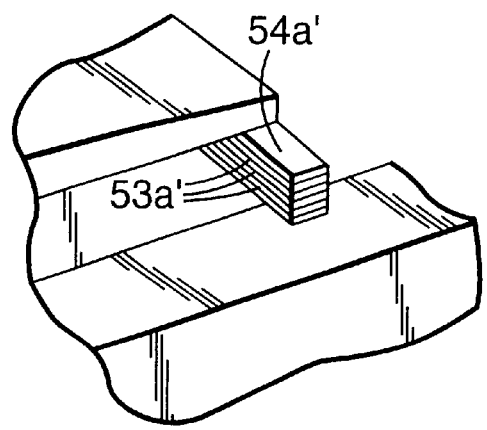
FIG. 6a is an enlarged cross-sectional perspective view of a portion of the appliance and archwire depicted in FIG. 6 but showing an alternative latch construction.

FIG. 6a illustrates an alternative arm portion 54a' that may be used if desired in place of the arm portions 54a depicted in FIG. 6. The arm portion 54a' as shown in FIG. 6a is made of a stack of discreet sections 53a' that move independently relative to each other. The stack may comprise 5, 10 or any other suitable number of sections 53a'. The use of discreet sections 53a' facilitates deflection of the arm portion 54a' in a labial or in a lingual direction when desired.

Figure 7:
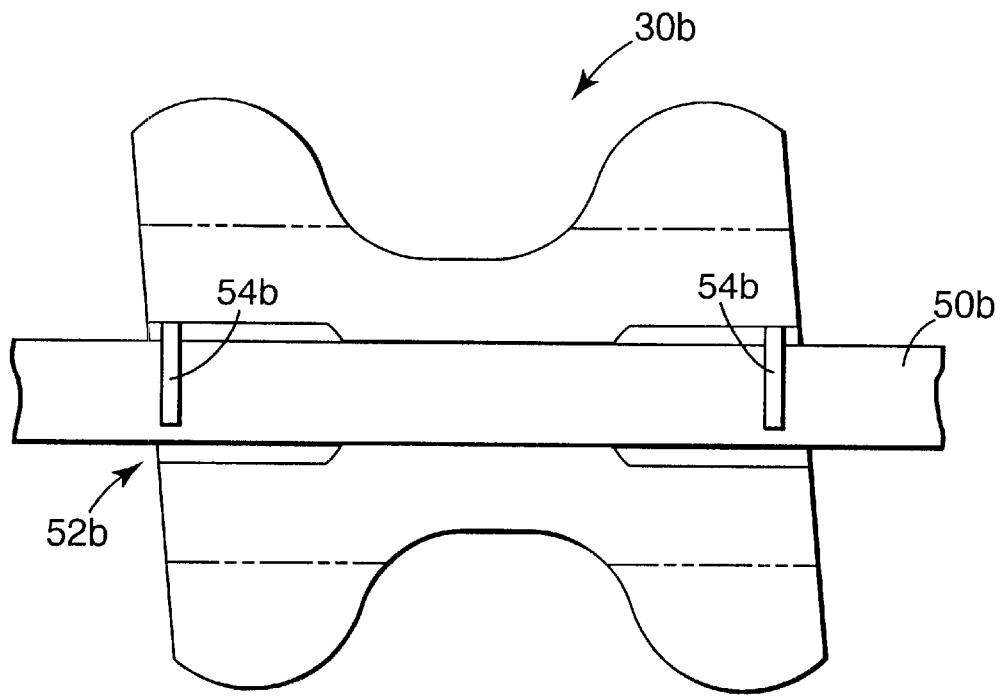
FIG. 7 is a view somewhat similar to FIG. 1 but illustrating an orthodontic appliance constructed in accordance with another embodiment of the invention.

An orthodontic appliance 30b according to another embodiment of the invention is shown in FIG. 7 in elevational view. The appliance 30b is similar to the appliance 30a, except for the differences noted below.

The appliance 30b has a latch 52b that includes two arm portions 54b. Each arm portion 54b extends across a labial side of an archwire 50b that is received in an archwire slot of the appliance 30b.

Preferably, each arm portion 54b extends across the labial side of the archwire 50b a distance that is greater than at least half of the occlusal-gingival dimension of the archwire 50b. In FIG. 7, the arm portions 54b are shown as descending in a gingival direction from an occlusal side of archwire slot relief areas, although as an alternative, the arm portions 54b could extend in an occlusal direction from a gingival side of each archwire slot relief area. The arm portions 54b may be made of a single, solid section of wire, or alternatively may each be made of a number of sections arranged in a stacked array similar to the arm portion 54a' illustrated in FIG. 6a.

Figure 8:
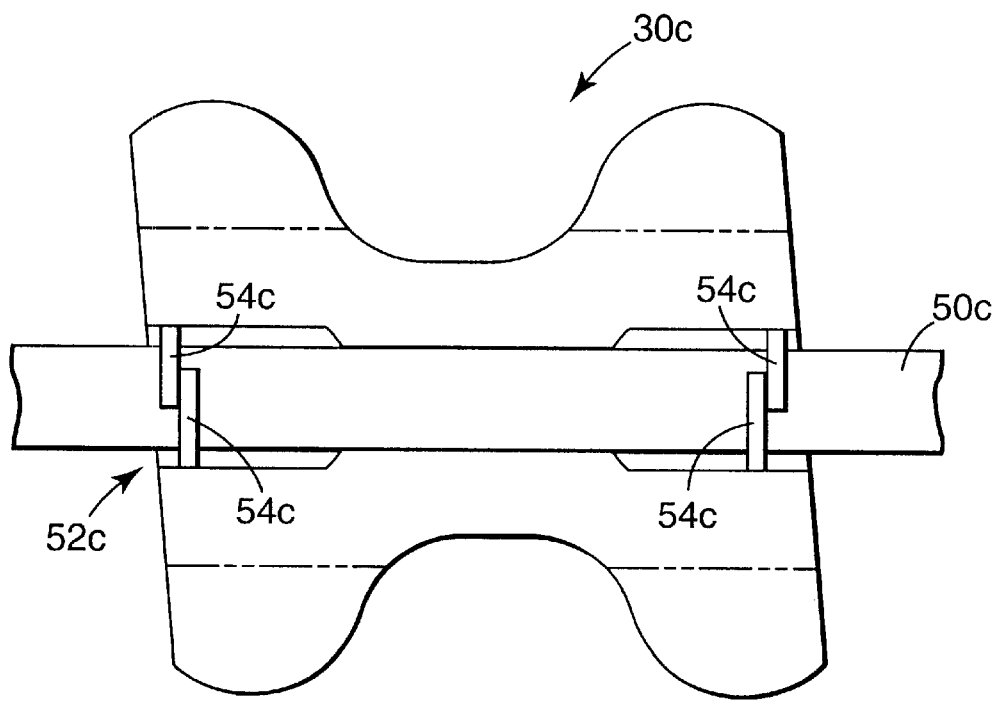
FIG. 8 is view somewhat similar to FIG. 1 but illustrating an orthodontic appliance constructed in accordance with yet another embodiment of the invention.

An orthodontic appliance 30c that is constructed in accordance with another embodiment of the invention is illustrated in FIG. 8. The appliance 30c is similar to the appliance 30a, except for the differences as set out below.

The appliance 30c includes a latch 52c having four arm portions 54c. The arm portions 54c are somewhat similar to the arm portions 54a, except that the arm portions 54c are somewhat longer and overlap each other. Additionally, the arm portions 54c that extend from an occlusal side of archwire slot relief areas are located laterally of arm portions 54c that extend from a gingival side of the archwire slot relief areas, although alternative constructions could be provided as well.

Optionally, and as shown in FIG. 8, each of the arm portions 54c extends a distance across a labial side of the archwire that is greater than one-half of the occlusal-gingival dimension of the labial side of the archwire. As another option, each arm portion 54c is made of a stack of discreet sections, similar to the sections 53a' as described above.

Figure 9:
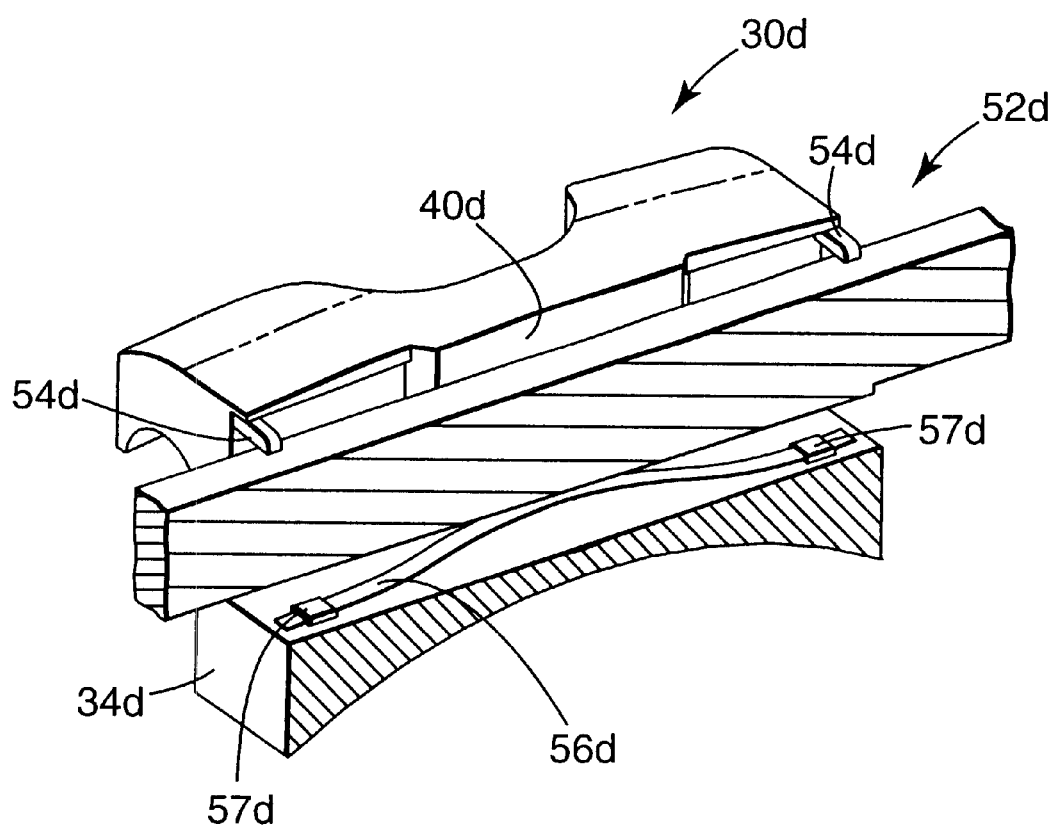
FIG. 9 is a view somewhat similar to FIG. 2 but showing an orthodontic appliance that is constructed in accordance with another embodiment of the invention.

An orthodontic appliance 30d according to another embodiment of the invention is illustrated in FIG. 9 in sectional view. The appliance 30d is similar to the appliance 30a, except for the difference as set out below.

The appliance 30d includes a latch 52d having a spring member 56d that is preferably made from an initially flat section of resilient metallic spring material. The spring member 56d has a mesial portion, a distal portion and a middle portion located between the mesial portion and the distal portion. Additionally, the spring member 56d is elongated and extends along the length of an archwire slot 40d of the appliance 30d.

The mesial portion and the distal portion of the spring member 56d are movably connected to a body 34d of the appliance 30d. In the embodiment illustrated, a pair of sleeves 57d are fixed to the body 34d, and each sleeve 57d receives either the mesial portion or the distal portion of the spring member 56d. However, alternative structures for connecting the spring member 56d to the body 34d may also be employed, including the provision of slots in the body 34d or headed pins connected to the body 34d that extend through slots in the mesial and distal portions.

The middle portion of the spring member 56d is normally located a distance spaced in a buccolabial direction from the mesial and distal portions, but can be moved in a lingual direction against the inherent bias of the spring member 56d when desired. For example, when an archwire is inserted into the archwire slot 40d, the middle portion of the spring member 56d can be shifted lingually a distance sufficient to enable the archwire to clear four arm portions 54d of the latch 52d, so that the arm portions 54d can return to their normally slot-closed position. Only two of the arm portions 54d are shown in FIG. 9, but it should be understood in this regard that the latch 52d has four arm portions 54d constructed and arranged in similar fashion to the arm portions 54a of the appliance 30a. Alternatively, the arm portions may be constructed differently (e.g., according to the other options described above).

The middle portion of the spring member 56d serves as a movable floor or tab that defines a lingual side of the archwire slot 40d. Once an archwire is received in the archwire slot 40d and the arm portions 54d have returned to their slot-closed position, the middle portion of the spring member 56d urges the archwire toward a position of engagement with the arm portions 54d (assuming that the selected archwire has a sufficient cross-sectional configuration to substantially fill the archwire slot 40d). The spring member 56d preferably engages the archwire during the course of treatment for active therapy in a central portion of the body 34d, and preferably engages the archwire in a location adjacent the parallel wall portions of the archwire slot 40d where precise control over movement of the appliance 30d and the associated tooth is provided.

An orthodontic appliance 30e according to another embodiment of the invention is depicted in FIGS. 10–13. The appliance 30e is essentially the same as the appliance 30a, except for the differences as described below.

The appliance 30e has a latch 52e for releasably retaining an archwire 50e (FIGS. 11–13) in an archwire slot 40e. The latch 52e has two pair of flexible arm portions 54e that are identical to the arm portions 54a. However, instead of an elongated, single spring member (such as spring member 56a or 56b) the latch 52e has two pair of spring members or tabs 55e that are located adjacent mesial and distal sides of a body 34e of the appliance 30e.

The tabs 55e are optionally similar in construction to the arm portions 54e or any of the other arm portions described above. For example, the tabs 55e may be made of a section of flexible round or rectangular wire material such as nitinol or stainless steel. The tabs 55e may be affixed to the body 34e by any suitable means, including drilling holes in the body 34e to receive a portion of the tabs 55e and then securing the tabs 55e in place by an interference fit, by welding or brazing, by fasteners or by an adhesive bond.

The tabs 55e have buccolabial wall portions that rest against the archwire 50e during treatment in use to define a lingual side of the archwire slot 40e. The tabs 55e also are movable in a lingual direction sufficiently to enable the archwire 50e to be latched into the archwire slot 40e when desired. FIG. 12 illustrates movement of the tabs 55e as the archwire 50e is placed into the archwire slot 40e. As shown, the tabs 55e deflect in a lingual direction and bend in an arc a distance sufficient to enable the archwire 50e to clear the opposed, facing ends of the arm portions 54e as the archwire 50e is pushed in a lingual direction. At that time, the arm portions 54e will spring back to their normal orientation to close the archwire slot 40e. The inherent bias of the tabs 55e to a normally straight configuration then functions to urge a buccolabial side of the archwire 50e into engagement with the lingual side of the arm portions 54e.

FIG. 11 is an illustration for exemplary purposes of the archwire 50e in the archwire slot 40e during the course of orthodontic treatment. As shown, the tabs 55e are normally straight and also serve to urge the archwire 50e in a buccolabial direction toward a position of contact with the arm portions 54e. The tabs 55e thus function to provide an active form of orthodontic treatment during the course of therapy.

FIG. 13 is an illustration of the appliance 30e as the archwire 50e is released from the archwire slot 40e. As shown, the arm portions 54e deflect outwardly to open the archwire slot 40e and enable the archwire 50e to disengage the appliance 30e. Preferably, and like the latch 52, the arm portions 54e of the latch 52e release the archwire 50e whenever the archwire 50e exerts a force in a generally buccolabial direction on the appliance 30e that exceeds a certain minimum value. Preferably, that minimum force is substantially less than about one-half of the force required in the same direction to debond the appliance 30e from the associated tooth.

As shown in the drawings, the space between the opposed, facing ends of the tabs 55e is less than the space between the opposed, facing ends of the arm portions 54e. Preferably, the space between the opposed, facing ends of the tabs 55e is sufficiently small so that those ends do not engage the occlusal and gingival sides of the archwire 50e when the archwire 50e has reached its limit of travel in a lingual direction. Such construction helps ensure that the tabs 55e will remain in engagement with the lingual side of the archwire 50e or its adjacent corners so that the tabs 55e can subsequently function to return the archwire 50e to the position shown in FIG. 11 in reliable fashion.

As further options, the arm portions 52e in FIGS. 10–13 as well as the arm portions 54b, 54c and 54d as shown in FIGS. 7–9 respectively can be made by bending a section of wire to a generally "U"-shaped configuration, where the bight of the "U" is substantially longer in length than the length of its legs. The bight is then fixed to the bracket body in such a manner that the legs project toward the archwire slot in an occlusal or gingival direction and present the arm portions. Optionally, the bight section can be received in a shallow groove of the appliance body adjacent a labial side of the archwire slot.

The tabs 55e as illustrated in FIGS. 10–13 may also be made according to the "U"-shaped configuration described in the preceding paragraph. Construction of the arm portions and tabs in this manner reduces the number of parts to be handled during manufacturing, and also avoids the need to insert arm portions or tabs into small holes of the body. As an additional option, the arm portions or the tabs made in such a manner may also be comprised of a stack of discreet, generally "U"-shaped sections in order to present a stacked array similar to the stacked sections 53a' illustrated in FIG. 6a.

Figure 14:
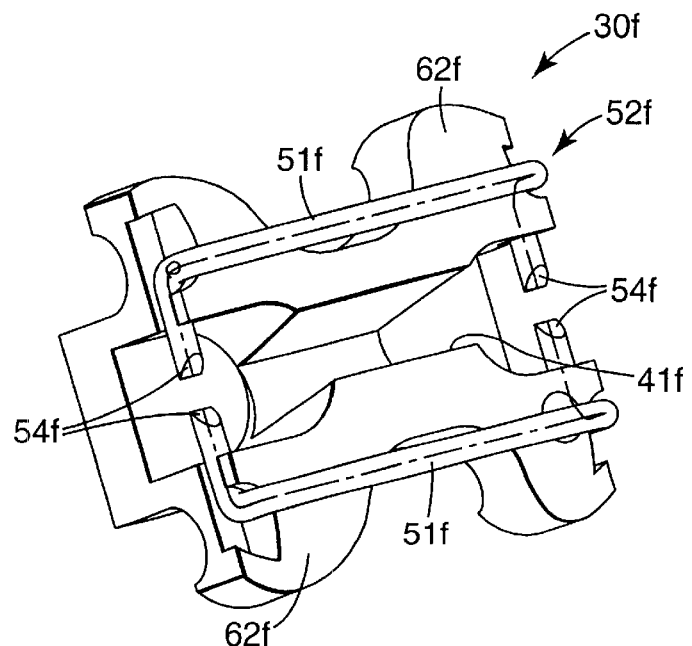
FIG. 14 is a perspective view of an orthodontic appliance according to another embodiment of the invention.

An orthodontic appliance 30f according to another embodiment of the invention is illustrated in FIG. 14. The appliance 30f is somewhat similar to the appliance 30e depicted in FIGS. 10–13 except for the differences noted below.

The appliance 30f includes a latch 52f that is comprised of a pair of opposed ligating members 51f, 51f. Each of the ligating members 51f has a generally "U"-shaped configuration in elevational view when viewed in a lingual direction. Each of the ligating members 51f has a pair of arm portions 54f, 54f, and the arm portions 54f of one ligating member 5 if are directly opposed to the arm portions 54f of the opposite ligating member 51f. Other constructions, however, are also possible.

Each of the ligating members 51f is slidable along a generally occlusal-gingival reference axis is a direction toward and away from an archwire slot 40f of the appliance 30f. Preferably, each arm portion 54f has a chamfered outer end, such that the ligating members 54f slide away from each other to a slot-open position when an archwire (not shown) is inserted into the archwire slot 40f. As an alternative, however, the practitioner may elect to use a dental probe or ligature director to engage a middle portion of each ligating member 51f and slide the same outwardly in order to open the latch 52f.

Optionally, the appliance 30f may be provided with lingual archwire slot tabs somewhat similar to the tabs 55e illustrated in FIGS. 10–13. The tabs in such an instance are movable in a lingual direction sufficiently to enable the archwire to be inserted into the archwire slot 41f by deflecting the arm portions 54f in a lingual direction. In such construction, the arm portions 54f and the tabs function in a manner similar to the arm portions 54e and the tabs 55e described above. As another option, an elongated spring member (such as spring member 56 or 56d) may be provided in place of the tabs.

The appliance 30f also includes four tiewings 62f. Each of the tiewings 62f is similar to the tiewings 62 described in connection with the embodiment shown in FIGS. 1–5, except that outer corners of the tiewings 62f have been constructed to provide for reception of the ligating members 51f and to enable limited sliding movement of the ligating members 51f when desired. The ligating members 51f may be made from a section of wire material such as stainless steel or nitinol.

Figure 15:
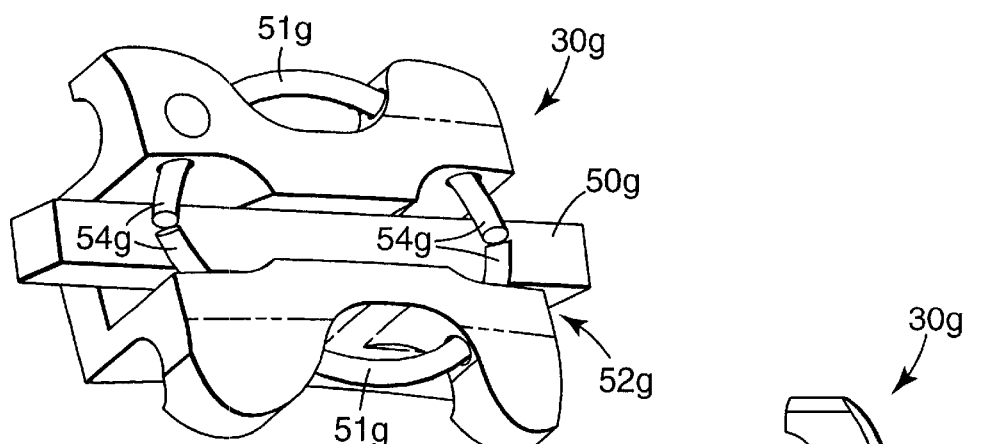
FIG. 15 is a perspective view of an orthodontic appliance constructed in accordance with still another embodiment of the invention, and additionally depicting an archwire that is received in an archwire slot of the appliance.
Figure 16:
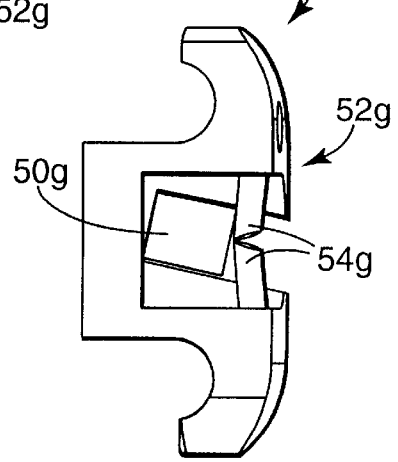
FIG. 16 is an end elevational view looking toward a mesial side of the appliance shown in FIG. 15 and showing the archwire in cross-section.

An orthodontic appliance 30g that is constructed according to yet another embodiment of the invention is shown in FIGS. 15 and 16 along with an archwire 50g that is received in an archwire slot of the appliance 30g. The appliance 30g is substantially the same as the appliance 30f, except for the differences as described below.

The appliance 30g has a pair of ligature members 51g that, in this embodiment, have an overall, generally semicircular configuration. Each of the ligature members 51g presents a pair of arm portions 54g that preferably have outer, chamfered ends. Each of the ligature members 51g extends through two passages that are located within tiewings of the appliance 30g.

The arm portions 54g move to admit the archwire 50g into the archwire slot of the appliance 30g. For example, a dental probe or ligature director may be inserted in the space between the tiewings on the occlusal or gingival side of the appliance 30g and the middle portion of the ligature members 51g, and then moved outwardly in order to move the arm portions 54g of that ligature member 51g into the passages. As another option, the arm portions 54g are deflected inwardly in a lingual direction as the archwire 50g is pushed into the archwire slot. The ligature member 51g may include crimps, stops or other structure to limit movement along the passages and avoid disengaging the appliance body. If desired, the appliance 30g may be provided with tabs similar to tabs 55e or with spring members similar to the spring members 56, 56d described above.

As another option, the ligature member 51g may be constructed to open the latch 52g whenever the middle portions of the ligature members 51g are squeezed together in directions toward the archwire slot. Optionally, the shape of the passages and/or the orientation of the passage may be modified to facilitate such opening movement. For example, the passages could be oriented in the occlusal-gingival directions, so that squeezing the middle portions together would cause the outer end portions 54g to retract into the passages. As another option, the passage could be elongated in mesial-distal directions in areas near the archwire slot relief areas, so that the arm portions 54g swing outwardly in distal directions when the middle portions are squeezed together. Any suitable hand instrument such as a pair of fine-tipped pliers may be used to squeeze the middle portions together. The latch 52g opens by deflection of the arm portions 54g outwardly as described above in connection with other embodiments.

Figure 17:
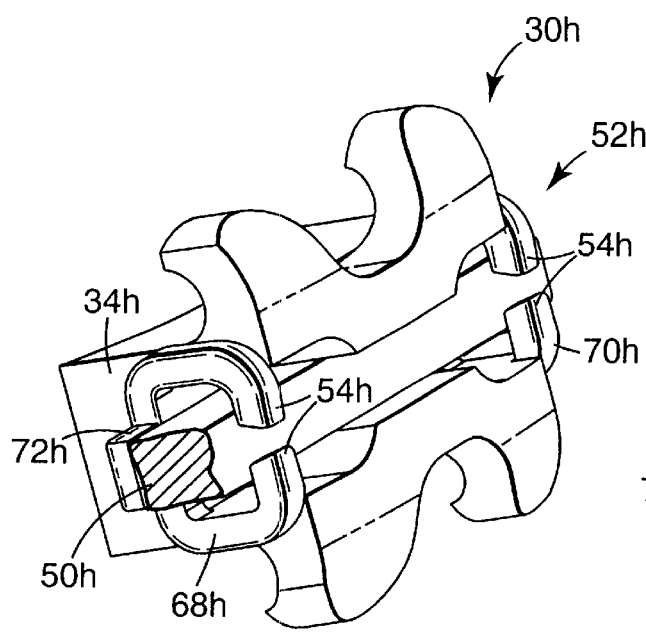
FIG. 17 is a perspective view of an orthodontic appliance constructed in accordance with still another embodiment of the invention along with an archwire received in an archwire slot of the appliance.
Figure 18:
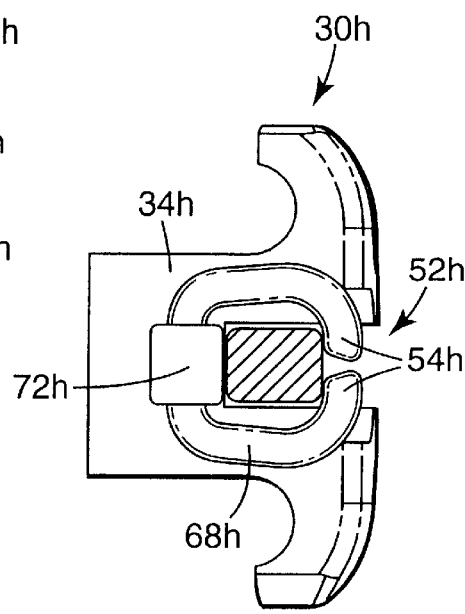
FIG. 18 is an end elevational view in partial cross-section looking toward a mesial side of the appliance of FIG. 17.

An orthodontic appliance 30h according to another embodiment of the invention is illustrated in FIGS. 17 and 18. The appliance 30h is essentially the same as the appliance 30 except for the differences described below.

The appliance 30h has a latch 52h that represents a variation of the earlier-described latches. The latch 52h comprises a mesial spring clip 68h and a distal spring clip 70h. The mesial spring clip 68h is fixed to a mesial side of a body 34h of the appliance 30h, while the distal spring clip 70h is fixed to a distal side of the appliance body 34h.

The clips 68h, 70h have an overall, generally "C"-shaped configuration and each includes a pair of arm portions 54h that extend toward each other. Preferably, each of the spring clips 69h, 70h is received in a sleeve 72h. The sleeve 72h is preferably fixed to a body 34h of the appliance 30h by a brazing or welding (including laser welding) process. The clip 68h and one sleeve 72h constitute a mesial assembly, and the clip 70h and the other sleeve constitute a distal assembly.

The sleeves 72h are an advantage in that the spring clips 68h, 70h may be made of a material that is difficult to weld or braze to the body 34h. For example, the clips 68h, 70h may be made of a resilient shape-memory alloy such as near-stoichiometric nitinol, while the body 34h may be made of an alloy of stainless steel. In that instance, the sleeve 72h may be also made of an alloy of stainless steel that can be readily welded or brazed to the body 34h according to conventional welding or brazing techniques. The sleeve 72h thus serves to couple the spring clips 68h, 70h to the body 34h.

The clips 68h, 70h including the arm portions 54h are sufficiently resilient to enable an archwire 50h to be inserted into an archwire slot by urging the archwire 50h in a lingual direction into the space within the confines of the clips 68h, 70h. As the archwire 50h engages the arm portions 54h, the clips 68h, 70h self-deflect and spread open a distance sufficient to enlarge the space between the arm portions 54h and allow the archwire 50h to pass through that space. Once the archwire 50h is received within the confines of the clips 68h, 70h, the clips 68h, 70h spring back to their normal orientation as shown in FIGS. 17 and 18 to retain the archwire 50h in the archwire slot.

The clips 68h, 70h including the arm portions 54h are sufficiently stiff to retain the archwire 50h in the archwire slot during the course of treatment so long as forces exerted by the archwire 50h on the appliance 30h are below a certain minimum value in a generally buccolabial direction (more particularly, in a direction opposite to the direction of insertion of the archwire 50h into the archwire slot). However, whenever the forces exerted by the archwire 50h on the appliance 30h in the same direction are greater than the minimum value, as might occur when unexpectedly high forces are encountered, the arm portions 54h deflect outwardly and the clips 68h, 70h open to enable the archwire 50h to be released from the archwire slot. In this manner, the appliance 30h does not unintentionally debond from the tooth when unexpected, relatively high forces are encountered.

The shape of the outer ends of the arm portions 54h may be modified to enhance insertion or release of the archwire 50h as desired. For example, the outer, buccolabial corners of the arm portions 54h may be curved or tapered to facilitate spreading the clips 68h, 70h apart during insertion of the archwire 50h into the archwire slot. However, to ensure that the arm portions 54h do not spread apart until forces exerted by the archwire 50h exceed the minimum value, the facing end sections of the arm portions 54h may be cut at an angle or extended toward each other as needed.

Figure 19:
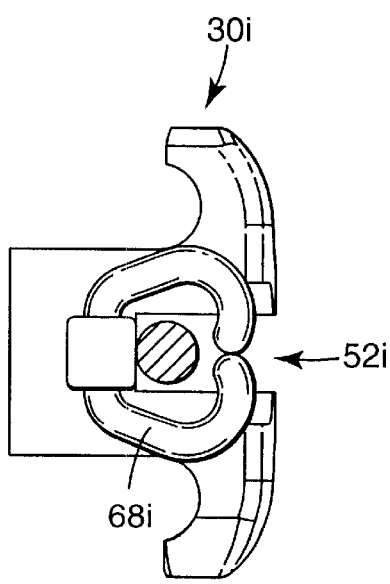
FIG. 19 is a view somewhat similar to FIG. 18 but showing an orthodontic appliance constructed in accordance with another embodiment of the invention.

An orthodontic appliance 30i according to yet another embodiment of the invention is illustrated in FIG. 19. The appliance 30i is essentially the same as the appliance 30h described above, except that the appliance 30i includes a latch 52i with a mesial spring clip 68i having a somewhat different shape than the mesial spring clip 68h shown in FIG. 18. The shape of the clip 68i may be an advantage in facilitating insertion of a smaller archwire 50i (such as an archwire having a circular cross-section as shown) in an archwire slot of the appliance 30i. The appliance 30i also has a distal spring clip that is not shown, but is essentially the same as the mesial spring clip 68i.

In the example shown in FIG. 19 the archwire is spaced from the clip 68i and as a result the appliance 30i provides passive orthodontic therapy. Optionally, the clip 68i can be constructed to engage the labial side of larger archwires, so that the appliance 30i in that instance provides active orthodontic therapy.

Figure 20:
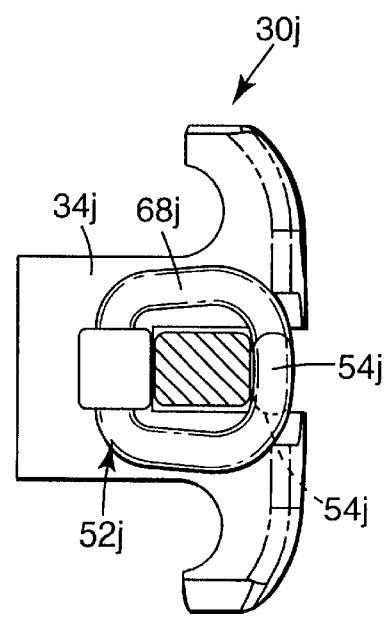
FIG. 20 is a view somewhat similar to FIG. 18 but showing an orthodontic appliance constructed in accordance with still another embodiment of the invention.

An orthodontic appliance 30j according to still another embodiment of the invention is illustrated in FIG. 20. The appliance 30j is essentially the same as the appliance 30h described in connection with FIGS. 17 and 18, except that the appliance 30j includes a latch 52j with a mesial spring clip 68j having a somewhat different shape than the mesial spring clip 68h shown in FIGS. 17 and 18. More particularly, the mesial spring clip 68j has a pair of arm portions 54j that overlap each other in directions along a mesial-distal reference axis and as shown by the dotted lines in FIG. 20. The appliance 30j has a distal spring clip that is not shown, but is identical to the mesial spring clip 68j and is optionally attached by a sleeve to a distal side of the appliance body.

Figure 21:
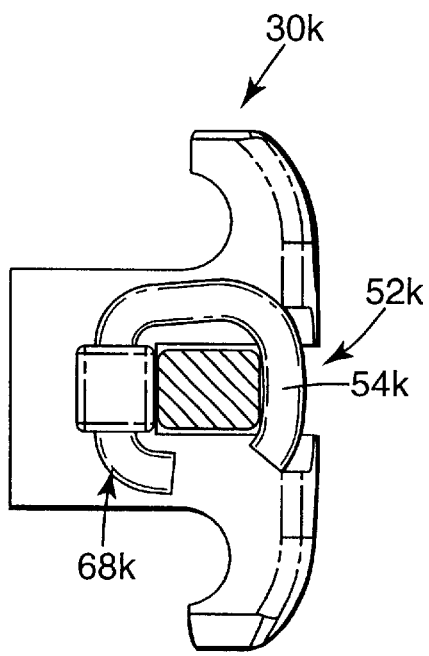
FIG. 21 is a view somewhat similar to FIG. 18 but showing an orthodontic appliance according to a further embodiment of the invention.

An orthodontic appliance 30k according to a further embodiment of the invention is illustrated in FIG. 21. The appliance 30k is essentially the same as the appliance 30h described above, except that the appliance 30k has a latch 52k with a mesial spring clip 68k having a generally "C"-shaped configuration. The mesial spring clip 68k presents only a single arm portion 54k that extends at least partially across, and preferably fully across the labial side of an archwire that is received in an archwire slot of the appliance 30k.

The appliance 30k also has a distal spring clip that is not illustrated in FIG. 21, but is essentially the same as the mesial spring clip 68k. The distal spring clip is optionally attached by a sleeve to a distal side of the body of the appliance 30k.

Figure 22:
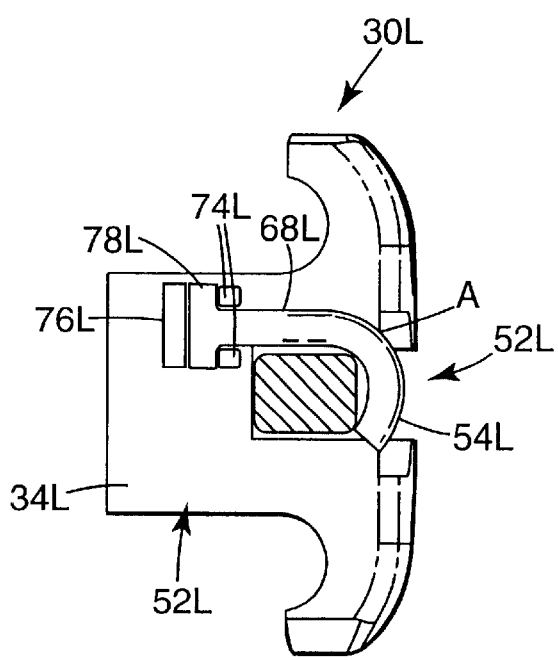
FIG. 22 is a view somewhat similar to FIG. 18 but showing an orthodontic appliance constructed according to an additional embodiment of the invention.

An orthodontic appliance 30L according to another embodiment of the invention is illustrated in FIG. 22. The appliance 30L is somewhat similar to the appliance 30h, except that the appliance 30L has a latch 52L that includes a mesial spring clip 68L having a generally overall "J"-shaped configuration. The mesial spring clip 68L also has only a single arm portion 54L that extends at least partially across, and preferably fully across a labial side of an archwire that is received in an archwire slot of the appliance 30L.

A bracket body 34L of the appliance 30L includes a pair of bosses 74L as well as a bar 76L. The bosses 74L and the bar 76L are preferably integrally connected with a body 34L of the appliance 30L and project outwardly in a mesial direction. The spring clip 68L has a lingual end portion 78L with a "T"-shaped configuration that fits snugly between the bosses 74L as well as the bar 76L in the manner depicted in FIG. 22.

Although not shown in the drawings, the appliance 30L includes a small mesial cap that covers the lingual end portion 74L of the mesial spring clip 68L. Preferably, the cap engages both of the bosses 78L as well as the bar 76L, and is secured to the bosses 74L and the bar 76L by a brazing operation, by a spot welding operation or the like. The cap, the bosses 74L and the bar 76L cooperate to securely fix the lingual end portion 78L of the mesial spring clip 68L to the mesial side of the appliance 30L.

The latch 52L also includes a distal spring clip that is not shown in the drawings, but is identical to the mesial spring clip 68L and is attached to the bracket body 34L in a similar manner. That is, the appliance 30L includes a pair of distally extending bosses and a distally extending bar that are connected to a distal side of the appliance 30L and are similar to the bosses 74L and the bar 76L respectively. Additionally, a cap is secured to the distal bosses and the distal bar in order to secure a lingual end portion of the distal spring clip to the distal side of the appliance body 34L.

Optionally, the spring clips of the appliances 30h–30L (including the spring clips 68h, 68L) are cut from a flat section of metallic stock material. Suitable metallic materials include shape memory alloys such as alloys of nitinol and beta-titanium. The spring clips may be cut from the stock material using a stamping, die cutting, chemical etching, EDM, laser cutting, or water jet cutting process. As another option, the clips could be formed and then heat treated to set their shapes. Advantageously, the clips and the sleeves of FIGS. 19 and 20 have mating, rectangular shapes in cross-sectional view so that the sleeves prevent pivotal movement of the clips relative to the appliance body about an occlusal-gingival axis.

A presently preferred clip is made from flat, annealed superelastic material having a pickled surface. The nitinol has a nickel content of 55.97 percent by weight and an $A_f$ of 10°±5° C. The nitinol is cold worked to 37.5% and has a thickness in the range of about 0.012 inch (0.3 mm) to about 0.016 inch (0.4 mm). The clip is first cut in a rough cutting EDM process, then cut along its edges for an additional one or more times using an EDM process in order to smooth the edges.

As another option, the spring clips of the appliances, and particularly the spring clips of the appliances 30h, are cut from a section of tubing that is made from a shape memory alloy. Suitable shape memory alloys include alloys of nitinol and beta-titanium. The tubing is cut with a slot to form the arm portions (such as the arm portions 54h).

As an additional option, the spring clips, the bracket bodies or other structure of the appliances 30h–30L are provided with a section of material that limits the degree of bending of the clip. For example, the clip 68L may have a small, labially extending section near an outer corner at the location designated "A". When the arm portion 54L is bent outwardly to open the latch 52L, the labially extending section prevents undue bending of the arm portion 54L so that the likelihood of damaging the clip 68L is reduced. As another example, the tiewings could have a small protrusion extending outwardly along a mesial-distal reference axis in the path of the clip in order to function as a stop and limit outward movement of the clip when the clip is opened.

In the appliances shown in FIGS. 17–20, the clips can be spread apart to different orientations in order to accommodate wires having different cross-sectional shapes. The clips also have inherent memory to repeatedly spring back to a closed position, so that occlusal and gingival sides of the clips are in contact with or closely adjacent the occlusal and gingival sides of the archwire respectively. Such construction provides better control over movement of the associated tooth.

Additionally, the clips of the appliances shown in FIGS. 17–24 preferably have a shape that facilitates opening of the latch when the archwire is pushed against the clip in a lingual direction. For example, the labial side of the clips preferably extends at an angle relative to an occlusal-gingival reference axis, so that the clip or at least the arm portion of the clip tends to deflect in a lateral direction (such as in an occlusal or in a gingival direction) as the archwire is urged in a lingual direction in order to open the latch and admit the archwire into the archwire slot.

Figure 23:
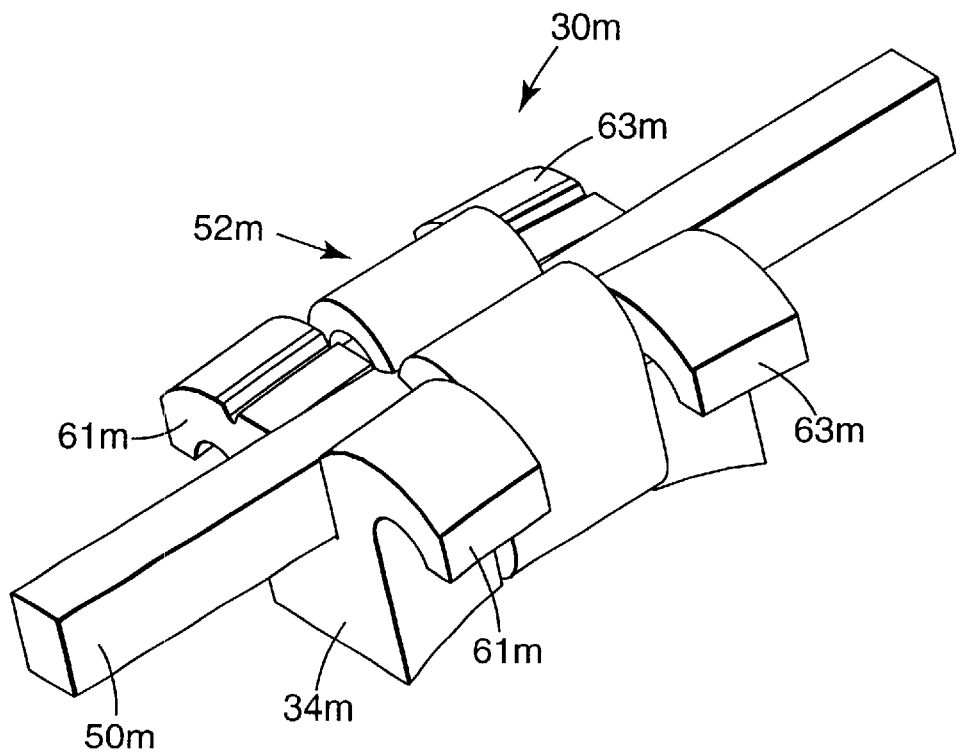
FIG. 23 is perspective view of an orthodontic appliance constructed according to yet another embodiment of the invention, along with an archwire that is received in an archwire slot of the appliance.
Figure 24:
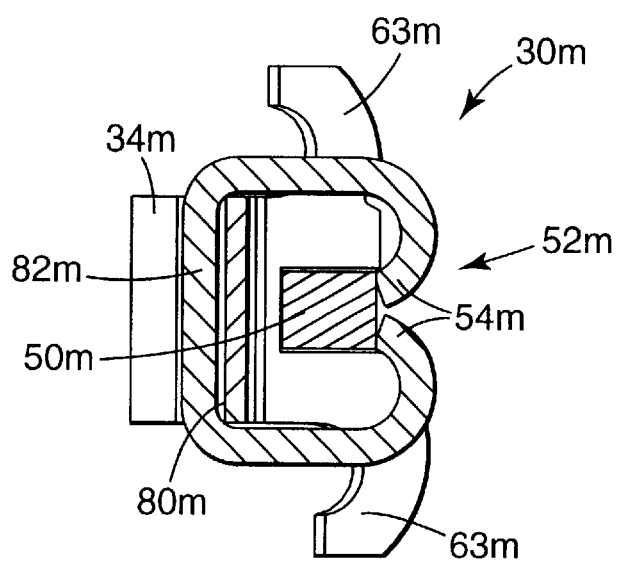
FIG. 24 is a cross-sectional view of the appliance and the archwire depicted in FIG. 23, and looking in a generally mesial-distal direction along a longitudinal axis of the archwire.

An orthodontic appliance 30m according to another embodiment of the invention is illustrated in FIGS. 23 and 24. The appliance 30m includes an appliance body 34m with a "twin tiewing" construction having mesial tiewings 61m that are spaced apart from distal tiewings 63m. The appliance body 34m also has a "vertical" channel 80m (FIG. 24) that is located lingually of an archwire slot of the appliance 30m and that extends in a generally occlusal-gingival direction.

The appliance 30m includes a latch 52m that is received in the space between the mesial tiewings 61m and the distal tiewings 63m. The latch 52m includes a lingual portion 82m that is received in the channel 80m. Although not shown in the drawings, the appliance 30m includes a base that is secured to a lingual side of the appliance body 34m, and the base captures the lingual portion 82m in the channel 80m in order to retain the latch 52m in secure connection to the body 34m.

The latch 52m includes a pair of arm portions 54m, each of which is shaped to engage a labial side of an archwire 50m when received in an archwire slot of the appliance 30m.

Each arm portion 54m has a somewhat "C"-shaped configuration, although other shapes are also possible. The "C"-shaped configuration as illustrated in FIG. 24 is an advantage, in that the arm portions 54m laterally deflect in occlusal and gingival directions respectively when the practitioner attempts to insert the archwire 50m into the archwire slot.

The latch 52m may be made of a section of resilient material such as stainless steel or nitinol. Other aspects of the appliance 30m are similar to the features of the appliances described above.

Figure 25:
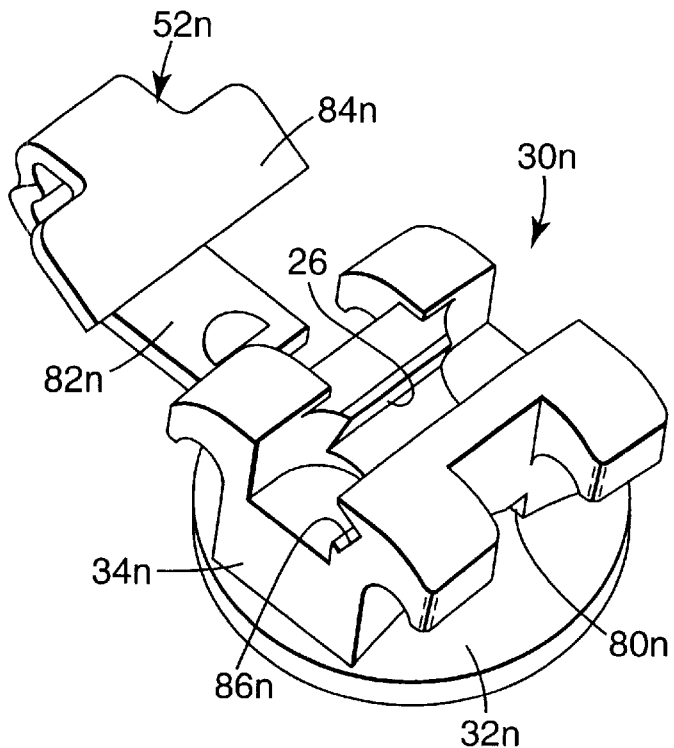
FIG. 25 is a perspective, exploded view of an orthodontic appliance that is constructed in accordance with another embodiment of the invention.
Figure 26:
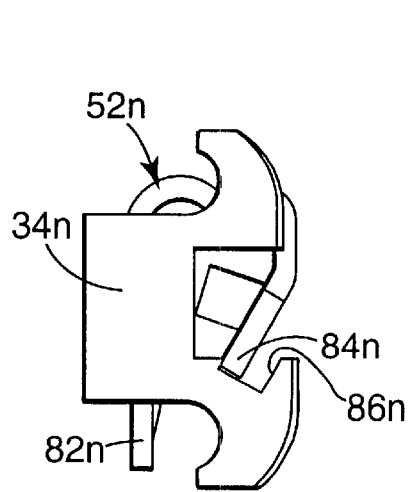
FIG. 26 is an end elevational view of the appliance shown in FIG. 25, wherein a latch of the appliance is illustrated in a slot-closed position.
Figure 27:
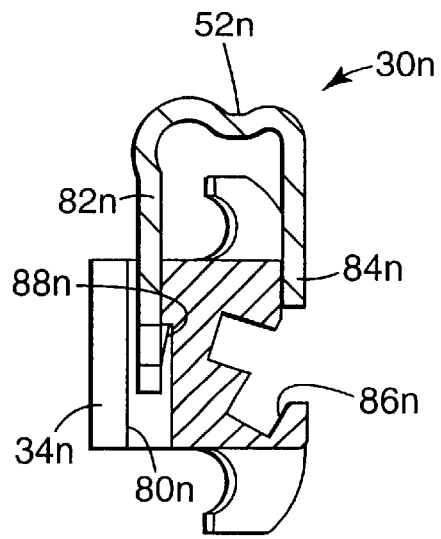
FIG. 27 is a cross-sectional view of the appliance shown in FIGS. 25 and 26, except that the latch has been moved to a slot-open position.

Another embodiment of the invention is shown in FIGS. 25–27, wherein an orthodontic appliance 30n according to the invention includes a bracket body 34n and a latch 52n. The latch 52n has a generally "U"-shaped configuration, and a lingual portion 82n of the latch 52n is received in a channel 80n (FIG. 27) of the appliance body 34n.

The appliance 30n is shown in exploded form in FIG. 25, where the latch 52n is separated from the appliance body 34n. FIGS. 26 and 27 illustrate the appliance 30n as it appears once the latch 52n has been assembled to the appliance body 34n.

The latch 52n is movable relative to the body 34n in a generally occlusal-gingival direction along the length of the channel 80n. In FIG. 26, the latch is shown in a slot-closed position wherein a labial end portion 84n of the latch 52n is received in an elongated cavity 86n.

In FIG. 27, the latch 52n is shown in a slot-open position that enables insertion or removal of an archwire from the archwire slot of the bracket. The lingual portion 82n of the latch 52n includes a protrusion 88n that engages a shoulder in the channel 80n to limit further movement of the latch 52n in an occlusal direction. As such, the protrusion 88n substantially prevents the latch 52n from unintentionally separating from the body 34n.

The appliance 30n also includes a base 32n that is fixed to the appliance body 34n by a brazing operation, by a tech-welding operation or by other suitable means. The base 32n is shown in FIG. 25 but is omitted in FIGS. 26 and 27. The base 32n serves to secure the appliance 30n to the patient's tooth surface, and also functions to capture the lingual portion 82n of the latch 52n in the channel 80n in order to retain the latch 52n in connected relationship to the body 34n.

The latch 52n is constructed so that the labial portion 84n is released from the cavity 86n and deflects outwardly in a labial direction whenever the archwire exerts a force on the latch 52n greater than a certain minimum value in a generally buccolabial direction that is substantially parallel with occlusal and gingival sides of the archwire slot. The minimum value is described above, and is significantly less than the force required in the same direction to debond the appliance 30n from the tooth. To this end, the length of the labial portion 84n that is received in the cavity 86n, and the geometry and bending strength of the latch 52h are selected so that the latch 52n reliably opens when the selected minimum value is exceeded. The latch 52n opens in this manner by outward bowing of the labial portion 84n and is ultimately released from the cavity 86n without movement of the latch 52n in an occlusal direction (i.e., without movement toward the orientation as shown in FIG. 27).

In other respects, the appliance 30n is similar to the orthodontic appliance described in applicant's U.S. Pat. No. 6,193,508, entitled "SELF-LIGATING ORTHODONTIC BRACKET WITH ENHANCED ROTATION CONTROL", which is incorporated by reference herein.

Figure 28:
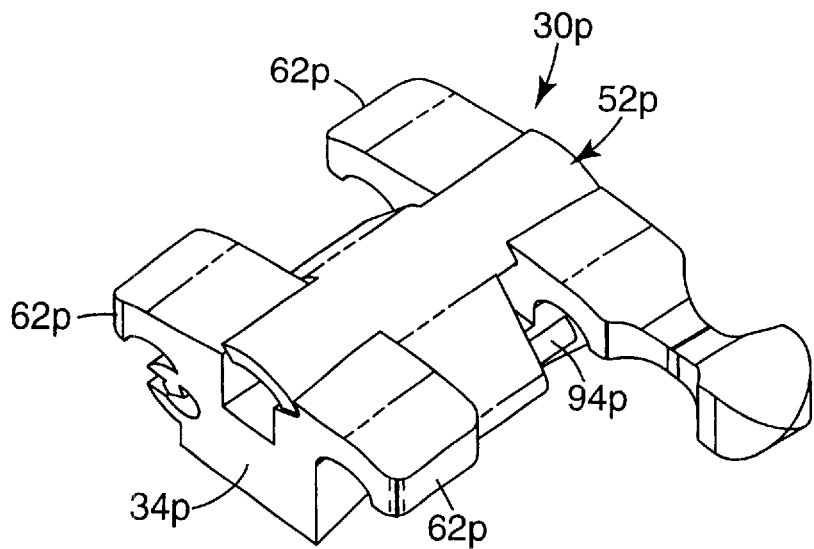
FIG. 28 is a perspective view of an orthodontic appliance according to a further embodiment of the invention.
Figures 29, 30:
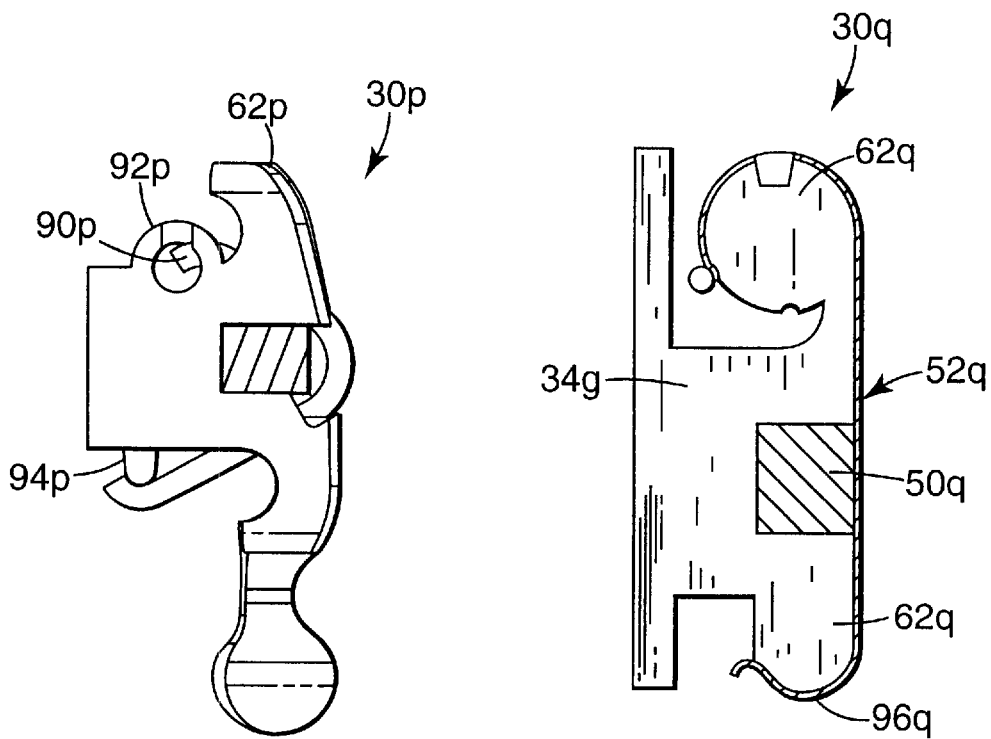
FIG. 29 is an end elevational view of the appliance depicted in FIG. 28 and looking toward a mesial side of the appliance, and additionally illustrating an archwire that is received in an archwire slot of the appliance.
FIG. 30 is an end elevational view of an orthodontic appliance that is constructed according to yet another embodiment of the invention.

An orthodontic appliance 30p according to another embodiment of the invention is illustrated in FIGS. 28 and 29. The appliance 30p includes a latch 52p that is pivotally connected to an appliance body 34p. As shown in FIG. 29, the latch 52p includes an occlusal end section or cross bar 90p that is received in passages of two cylindrical hinge sections 92p, one of which is shown in FIG. 29. Each of the hinge sections 92p is located lingually beneath a respective tiewings 62p.

The appliance body 34p includes an elongated, protruding catch 94p. The latch 32p includes a gingival end section that is curved to form a notch. When the latch 52p is in a closed position as illustrated in FIGS. 28 and 29, the notch engages the catch 94p and retains an archwire in an archwire slot of the appliance body 34p.

When the practitioner desires to open the latch 52p, the practitioner may place a dental probe, explorer or other fine-tipped hand instrument on the gingival portion of the latch 52p in order to deflect the gingival portion in a gingival direction and disengage the catch 94p. At that time, the latch 52p can be pivoted about the central axis of the hinge sections 92p in order to open the latch 52p and enable the archwire to be released from the archwire slot.

However, if the archwire exerts a force on the latch 52p of sufficient magnitude, the labial portion of the latch 52p will automatically disengage the catch 94p and allow the latch 52p to self-open. The latch 52p releases the archwire from the archwire slot whenever the archwire exerts a substantial force on the latch 52p so that the appliance 30p is not unintentionally debonded from the tooth. Preferably, the latch 52p opens whenever the force exerted by the archwire exceeds a certain minimum value as described above.

A variety of methods can be employed to ensure that the latch 52p opens whenever the archwire has exerted a force on the latch 52p of sufficient magnitude. For example, the shape of the notch of the occlusal portion of the latch 52p, as well as the shape of the catch 94p, may be altered as needed to vary the amount of force necessary to open the latch 52p. As another example, the material of the latch 52p may vary in composition or processed according to different conditions to ensure that the latch 52p consistently deforms whenever the desired minimum force of the archwire on the latch 52p has been exceeded.

As another alternative, the appliance 30p could be constructed so that the latch 52p is fixed on one end and bends when opened. Optionally, a lingual side of the latch could be fixed to a side of the appliance body, or within a lingual channel (not shown) of the body somewhat similar to the channel 80n shown in FIGS. 25–27. The opposite side of the latch in that instance would have a notch, groove, curve or some other shape adapted to releasably engage a cavity (such as cavity 86n), a protrusion or some other feature of the appliance.

An orthodontic appliance 30q according to another embodiment of the invention is illustrated in FIG. 30, and includes an appliance body 34q as well as a swingable latch 52q. In this embodiment, the latch 52q is pivotally connected to a tiewings 62q of the appliance body 34q.

The latch 52q includes an occlusal portion 96q that is releasably received over an occlusal tiewing 62q of the appliance body 34q. The occlusal portion 92q and the outer end of the occlusal tiewing 62q preferably have mating, curved shapes. When the latch 52q is in the position illustrated in FIG. 30, the latch 52q serves to retain an archwire 50q in an archwire slot of the appliance body 34q.

The latch 52q and the appliance body 34q are constructed to enable the latch 52q to move to a slot-open position whenever the force exerted by the archwire 50q in a buccolabial direction exceeds a certain minimum value. Preferably, the minimum value is the same as the minimum values described above. The latch 52q may also be manually opened by use of a dental probe, explorer or other hand instruments to deflect and disengage the occlusal portion 92q from the occlusal tiewings 62q.

Figure 31:
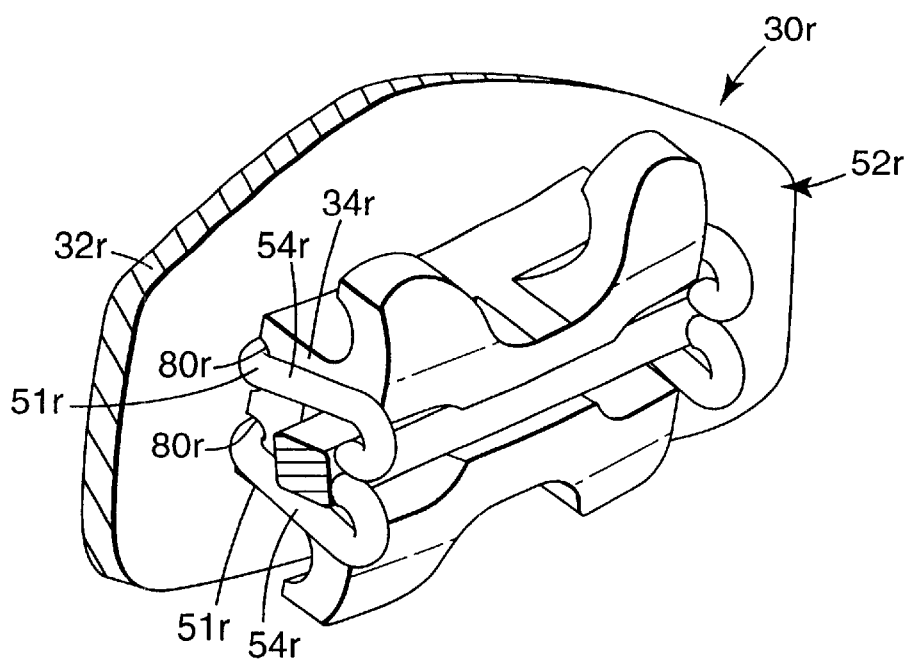
FIG. 31 is a perspective view of an orthodontic appliance constructed in accordance to a further embodiment of the invention.

FIG. 31 is an illustration of an orthodontic appliance 30r according to another embodiment of the present invention. As shown, the appliance 30r has a body 34r that is preferably identical to the body 34, except that the body 34r includes two, spaced-apart channels 80r along its lingual side. A latch 52r includes two ligating members 51r, 51r that have a generally "U"-shaped configuration when viewed along an occlusal-gingival reference axis. Each ligating member 51r has on opposite sides a pair of outer arm portions 54r, each of which includes a loop-shaped section.

The appliance 30r also includes a base 32r that, once fixed to the appliance body, serves to secure a lingual portion of the ligating members 51r in the channels 80r. Optionally, the channels 80r and the ligating members 51r have mating, rectangular or square cross-sectional configurations when viewed in directions perpendicular to their longitudinal axis, so that the lingual portion of each ligating member 51r will not pivot within the channels 80r. Optionally, the base 32r and the lingual portions of both ligating members 80r are welded, brazed or otherwise fixed to the appliance body in order to prevent pivotal movement of the ligating members 51r within the channels 80r.

The ligating members 51r are preferably made from resilient wire stock such as the stainless steel wires or wires made of the shape memory alloys described above. To open the latch 52r, the arms portions 54r spread apart and swing away from each other in opposite directions along mesial and distal sides of the appliance body. The latch 52r self-opens to admit or release an archwire whenever forces exerted by the archwire on the loop sections exceeds certain values, similar to the latches described above. The loop sections may be used to receive a hand instrument (such as a probe or fine tips of pliers) for manual opening of the latch 52r when desired.

Figure 32:
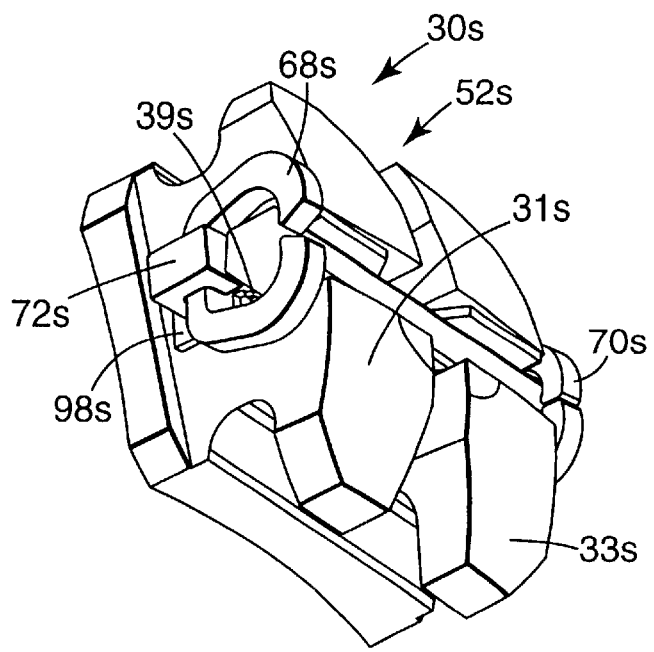
FIG. 32 is a perspective view of an orthodontic appliance that is constructed in accordance with still another embodiment of the invention.

An orthodontic appliance 30s that is constructed according to another embodiment of the invention is depicted in FIG. 32. The appliance 30s includes aesthetic ceramic mesial and distal body sections 31s, 33s respectively and is somewhat similar to the appliances described in U.S. Pat. Nos. 5,439,379 and 5,366,372, both of which are expressly incorporated by reference herein. The appliance 30s also includes an metallic archwire slot liner 39s that defines an archwire slot 40s. Examples of suitable materials and methods of constructing the archwire slot liner 39s, as well as examples of suitable methods for attaching the archwire slot liner 39s to the body sections 31s,33s are described in U.S. Pat. Nos. 5,358,402 and 5,380,196, both of which are also expressly incorporated by reference herein.

The archwire slot liner 39s includes a mesial segment 98s that extends along a mesial side of the mesial body section 31s in parallel relationship. Preferably, the mesial segment 98s is secured to the mesial side of the body section 31s by use of the methods described in U.S. Pat. Nos. 5,358,402 and 5,380,196. The mesial segment 98s serves as a mount for receiving a sleeve 72s of a latch 52s. The sleeve 72s is similar to the sleeve 72h described above and serves to couple a mesial spring clip 68h to the mesial body section 31s.

The clip 68s that is illustrated for exemplary purposes in FIG. 32 is similar to the clip 68h, although other clips such as the clips 68i–68L could alternatively be used. Additionally, the latch 52s includes a distal clip 70s that is secured by a distal sleeve to a distal segment of the archwire slot liner 39s. The distal sleeve and distal segment of the archwire slot liner 39s are not shown, but are similar to the mesial sleeve 72s and mesial segment 98s respectively. The latch 52s operates similarly to the latches described in the other embodiments above.

Figure 33:
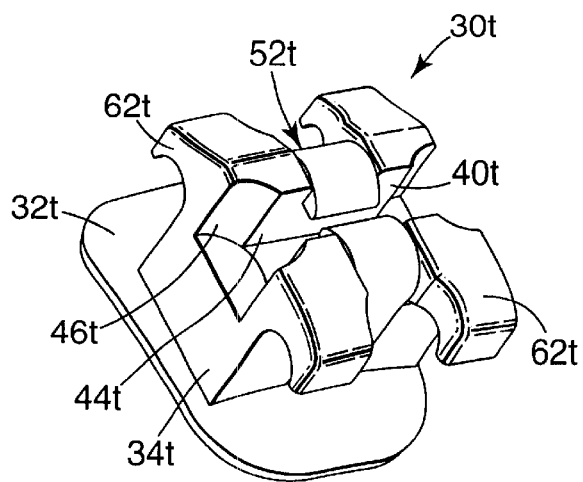
FIG. 33 is a perspective view of an orthodontic appliance that is constructed in accordance with an additional embodiment of the invention.
Figure 34:
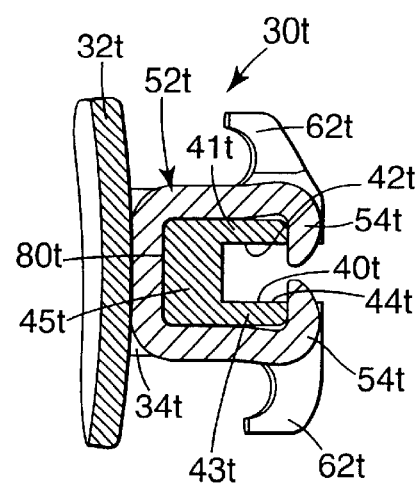
FIG. 34 is a cross-sectional view of the appliance depicted in FIG. 33, and looking in a generally mesial-distal direction along a longitudinal axis of an archwire slot of the appliance.
Figure 35:
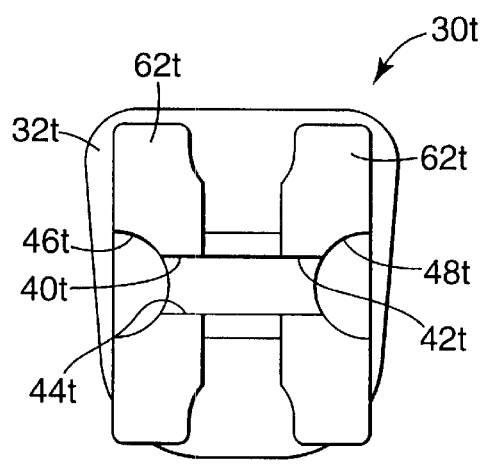
FIG. 35 is a front elevational view looking in a lingual direction toward the appliance shown in FIGS. 33 and 34 except that a latch of the appliance has been removed.

Another embodiment of the invention is depicted in FIGS. 33–35, wherein an orthodontic appliance 30t includes a base 32t and a body 34t that extends outwardly from the base 32t. The appliance 30t includes an archwire slot 40t that extends across the body 34t in a generally mesial-distal direction. The archwire slot 40t includes an occlusal side that is defined in part by a flat occlusal wall portion 42t and a gingival side as defined in part by a flat gingival wall portion 44t.

The appliance 30t also includes a mesial archwire slot relief area 46t and a distal archwire slot relief area 48t. The relief areas 46t, 48t function in a manner similar to the relief areas 46, 48 described above.

The appliance 30t includes a latch 52t that preferably has a generally overall "C"-shaped configuration. As can be appreciated, for example, by reference to FIG. 34, the latch 52t includes two arm portions 54t that extend toward each other. When the latch 52t is closed as shown in FIGS. 33 and 34, a small gap is present between the facing terminal edges of the opposed arm portions 54t. The latch 52t is not shown in FIG. 35.

As shown in FIG. 34, the latch 52t includes an occlusal portion that is spaced from the archwire slot 40t by an occlusal wall section 41t, a gingival portion that is spaced from the archwire slot 40t by a gingival wall section 43t and a lingual portion that is spaced from the archwire slot 40t by a lingual wall section 45t. The wall sections 41t, 43t, 45t are part of the body 34t and extend between adjacent tiewing portions 62t, each of which is integrally connected to the body 34t. The lingual portion of the latch 52t is received in a channel 80t that extends between the lingual wall section 45t and the base 32t, although as another option the channel 80t could extend through the body 34t at a location spaced from the base 32t.

Other aspects of the appliance 30t are similar to the aspects of the appliances described above.

Figure 36:
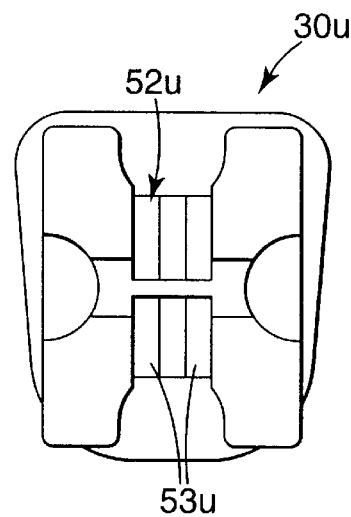
FIG. 36 is a front elevational view of an orthodontic appliance according to another embodiment of the invention.

An orthodontic appliance 30u according to another embodiment of the invention is illustrated in FIG. 36. The appliance 30u is essentially the same as the appliance 30t, except that the appliance 30u has a latch 52u that is comprised of more than one side-by-side section. In the embodiment illustrated, the latch 52u has three side-by-side sections 53u, although a smaller or greater quantity of sections is also possible.

Each of the latch sections 53u has arm portions that are movable independently relative to arm portions of the adjacent latch section 53u. Such construction may be an advantage in certain instances, such as when it is desired to reduce the stiffness of the arm portions. This construction may facilitate opening of the latch 52u and closing of the latch 52u, since each section 53u is movable independently of movement of the adjacent sections 53u.

If desired, each of the latch sections 53u may have identical cross-sectional configurations, such as the configuration of the latch 52t illustrated in FIG. 34. As another option, the latch sections 53u may be manufactured by cutting slots in a single latch (such as the latch 52*t*) in labial regions, so that the latch remains joined together in lingual regions. As a further option, the terminal edges of the arm portions of the latch sections 53*u* may be beveled in different fashions and/or have different configurations, so that the arm portions of one section tend to move before movement of the arm portions of the adjacent section in order to facilitate insertion or removal of an archwire from the archwire slot.

Figure 37:
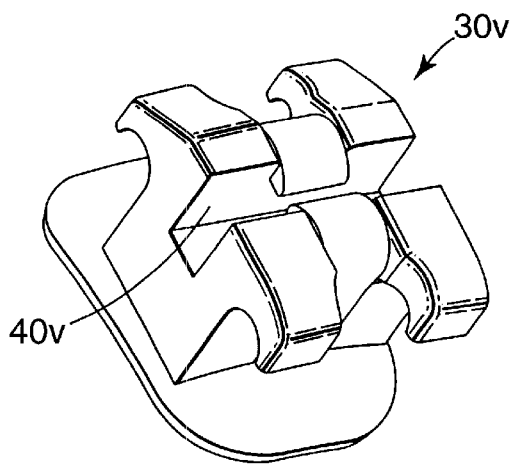
FIG. 37 is a perspective view of an orthodontic appliance according to still another embodiment of the invention.

An orthodontic appliance 30*v* according to yet another embodiment of the invention is illustrated in FIG. 37. The appliance 30*v* is essentially the same as the appliances 30*t*, 30*u*, except that the appliance 30*v* does not include archwire slot relief areas (such as relief areas 46*t*, 48*t*). Instead, the appliance 30*v* has an archwire slot 40*v* that is defined by precision archwire-engaging walls that extend from a mesial side of the appliance 30*v* to a distal side of the appliance 30*v* for engagement with an archwire (not shown).

Figure 38:
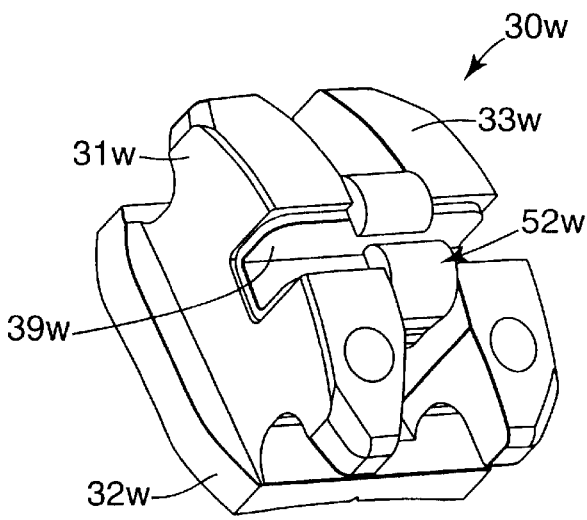
FIG. 38 is a perspective view of an orthodontic appliance according to yet another embodiment of the invention.
Figure 39:
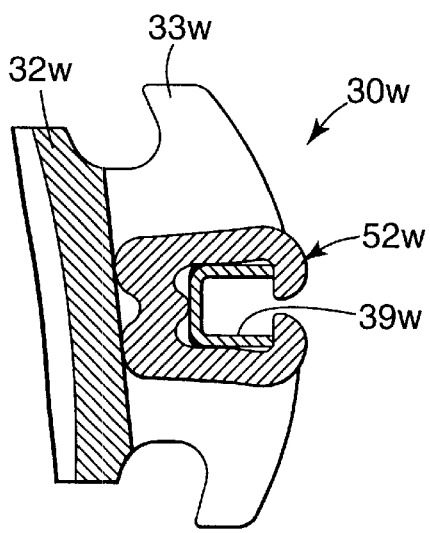
FIG. 39 is a cross-sectional view of the appliance depicted in FIG. 38, looking in a generally mesial-distal direction along a longitudinal axis of an archwire slot of the appliance.

An orthodontic appliance 30*w* according to a further embodiment is illustrated in FIGS. 38 and 39. The appliance 30*w* preferably includes aesthetic ceramic mesial and distal body sections 31*w*, 33*w* respectively and is somewhat similar to the appliance 30*s* that is illustrated in FIG. 32.

The appliance 30*w* includes a central latch 52*w* that is located between the mesial and distal body sections 31*w*, 33*w*. As shown in FIG. 39, the latch 52*w* extends about an occlusal, a lingual and a gingival side of a metallic archwire slot liner 39*w*. In this embodiment, the latch 52*w* extends parallel to the occlusal and gingival sides of the archwire slot liner 39*w*, and presents a "W"-shaped configuration adjacent a lingual side of the archwire slot liner 39*w*.

Although not shown in the drawings, the latch 52*w* may be positioned in place by providing an elongated hole in a base 32*w* of the appliance 30*w*, and then moving the latch 52*w* through the hole and spreading the latch 52*w* apart until it extends around the archwire slot liner 39*w* as shown in FIG. 39. The hole may then be filled, if desired, by a curable material that bonds to the ceramic material. An example of a suitable curable material is epoxy. Optionally, the curable material is colorless and transparent or relatively translucent when hardened so that it does not unduly detract from the aesthetic qualities of the ceramic material.

Preferably, the overall mesial-distal width of the latch 52*w* is somewhat smaller than the space between the mesial and distal body sections 31*w*, 33*w* so that the appliance 30*w* can be debonded by squeezing the sections 31*w*, 33*w* together as described in U.S. Pat. Nos. 5,439,379 and 5,366,372. As an additional option, the latch 52*w* may be provided with one or more sections, similar to the latch sections 53*u* described above. Other aspects of the appliance 30*w* could be similar, if desired, to the appliances described above.

Figure 40:
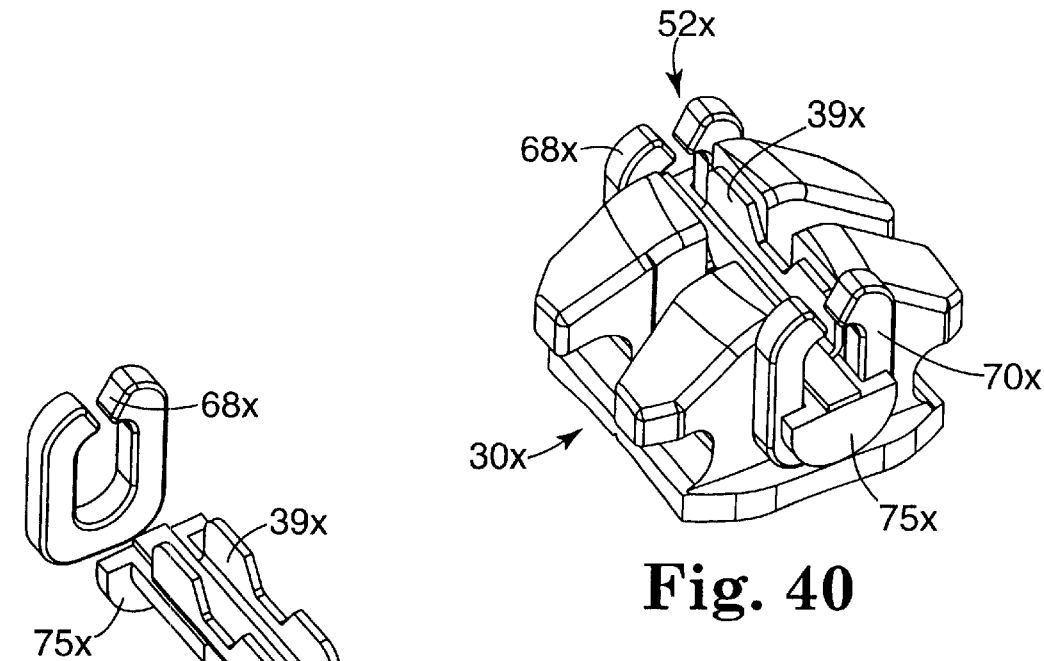
FIG. 40 is a perspective view of an orthodontic appliance according to still another embodiment of the invention.
Figure 41:
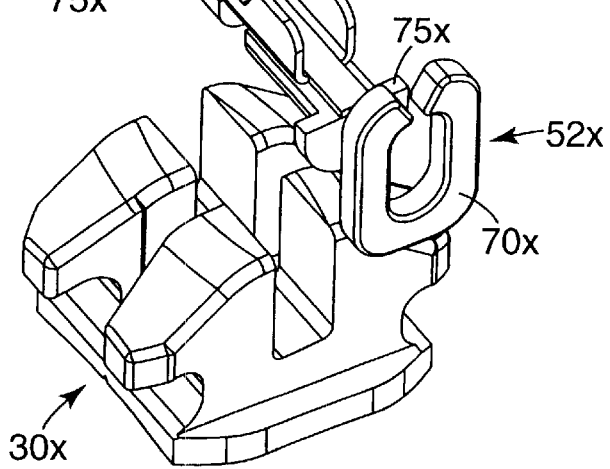
FIG. 41 is an exploded, perspective view of the orthodontic appliance shown in FIG. 40.

An orthodontic appliance 30*x* according to another embodiment of the invention is illustrated in FIGS. 40 and 41. The orthodontic appliance 30*x* is somewhat similar to the appliance 30*s* that is depicted in FIG. 32, except for the differences set out below.

The appliance 30*x* includes an archwire slot liner 39*x* as well as a pair of protrusions 75*x*. Each of the protrusions 75*x* is affixed to the liner 39*x* using, for example, an adhesive or a brazing or welding process. Optionally, the liner 39*x* is omitted and the protrusions 75*x* are affixed directly to the body of the appliance 30*x*. As another option, the liner 39*x* and the protrusions 75*x* could be molded or machined together as a single, unitary component. The protrusions 75*x* are spaced apart from each other in order to enable the appliance 30*x* to be debonded in the manner set out in the above-mentioned U.S. Pat. Nos. 5,439,379 and 5,366,372.

The orthodontic appliance 30*x* includes a latch 52*x* that comprises a mesial spring clip 68*x* and a distal spring clip 70*x*. The clips 68*x*, 70*x* are retained in place by an external flange of the protrusions 75*x* having a generally semicircular shape. The lingual side of the clips 68*x*, 70*x* is adjacent a base of the appliance 30*x*, so that the clips 68*x*, 70*x* cannot be inadvertently detached from the appliance 30*x* by movement in a lingual direction.

Optionally, the mesial and distal sections of the appliance 30*x* are made of a ceramic material, and the slot cut in the ceramic material to receive the archwire slot liner 39*x* has a stepped configuration. In that instance, the protrusions 75*x* have a width sufficiently narrow to be received in the bottom of the ceramic slot, while the overall width of the archwire slot liner 39*x* is somewhat wider and rests against the bottom of the steps during assembly. The steps function to hold the archwire slot liner 39*x* in a proper labial-lingual orientation until such time as the archwire slot liner 39*x* is fixed to the mesial and distal sections.

Figure 42:
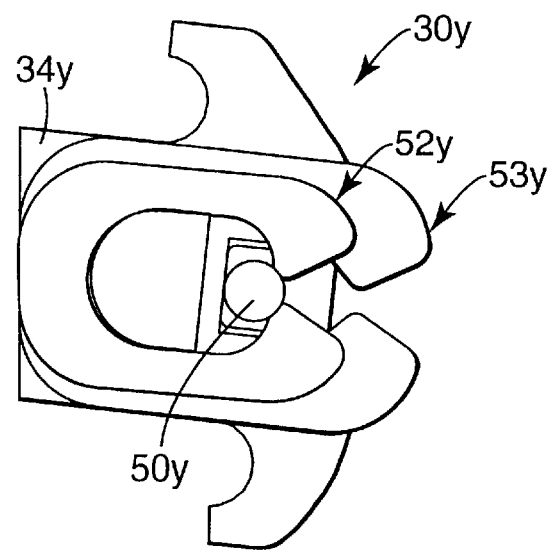
FIG. 42 is an end elevational view of another orthodontic appliance constructed according to the present invention.

FIG. 42 is an illustration of an orthodontic appliance 30*y* according to another embodiment of the invention. The appliance 30*y* has a first clip-type latch 52*y* and a second clip-type latch 53*y* adjacent the first latch 52*y*. The latch 53*y* extends further in a buccolabial direction than the latch 52*y* for retaining an archwire having a larger cross-sectional shape in a buccolabial direction.

Although not shown in the drawings, the latches 52*y*, 53*y* could be secured to the body 34*y* of the appliance 30*y* in a manner similar to that described in connection with the appliances 30*h*–30*k* depicted in FIGS. 17–21, and a pair of such latches 52*y*, 53*y* could be provided for both the mesial side and distal side of the body 34*y*. Alternatively, the latches 52*y*, 53*y* could be a single pair and located in the center of the appliance 30*y* in a manner similar to the location of the latch 52*m* shown in FIGS. 23–24. As yet another alternative, one of the latches 52*y*, 53*y* could be located in the center of the appliance 30*y* and a pair of the other latch 52*y* or 53*y* could be located on opposite sides of the appliance 30*y*.

The provision of two different latches 52*y*, 53*y* enables contact with archwires of varying sizes in order to assure active control over movement of the associated tooth. In FIG. 42 an archwire 50*y* has a relatively small cross-sectional area but is engaged and retained in the archwire slot by the latch 52*y*. If an archwire having a larger cross-sectional area was substituted for the archwire 50*y*, the larger archwire would be retained in the archwire slot by the larger latch 53*y*, while also in contact (along its occlusal and gingival sides) with the smaller latch 52*y*. In either instance, the archwire would be engaged by one or both of the latches 52*y*, 53*y* for active archwire therapy.

As another option, the appliance 30*y* could be provided with a series of three or more latches, at least three of which are of different sizes. In this manner, a wider variety of archwire sizes could be used to provide active archwire therapy. Such a series could include at least two spaced-apart clips of each size, so that good rotational control is provided for movement of the associated tooth.

In other respects, the appliance 30*y* is similar to the appliances 30*h*–30*k* and 30*m* described above. In FIG. 42, a base of the appliance 30*y* is not shown.

Figure 43A:
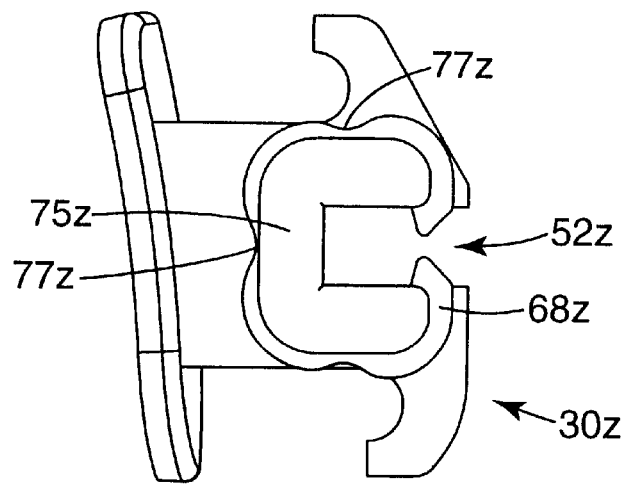
FIG. 43a is an end elevational view of an additional orthodontic appliance that is constructed in accordance with the present invention.
Figure 43B:
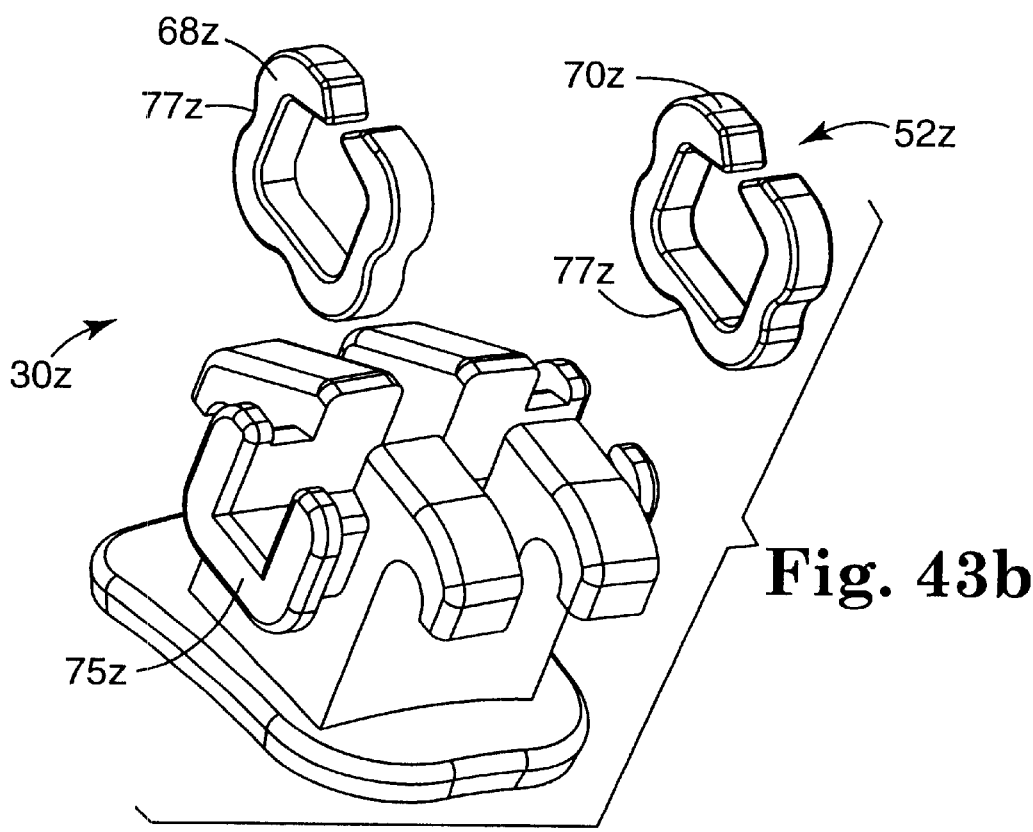

An orthodontic appliance 30*z* according to another embodiment of the invention is illustrated in FIGS. 43*a* and 43*b*. The orthodontic appliance 30*z* has protrusions 75*z* that extend outwardly in mesial and distal directions. More particularly, a mesial protrusion 75*z* extends in a mesial direction outwardly from a mesial section of the appliance 30z, while a distal protrusion 75z extends outwardly in a distal direction from a distal section of the appliance 30z.

Each of the protrusions 75z has a groove or channel that receives a spring clip 68z, 70z. The clips 68z, 70z comprise a latch 52z. Optionally, and as shown in the drawings, each of the clips 75z includes three notches 77z that facilitate opening and closing movements of the clips 68z, 70z.

The appliance 30z as shown in FIGS. 43a and 43b may be made of a variety of materials such as stainless steel or ceramic. Preferably, the protrusions 75z are integral with the adjacent mesial and distal sections respectively of the appliance 30z and form part of a single, unitary component. Suitable manufacturing techniques for making the appliance 30z include, for example, machining and molding (including metal injection molding).

Optionally, the appliances according to the invention, and particularly the appliances 30n, 30p and 30q illustrated in FIGS. 25–30, may be provided with a self-releasing latch that is movable from a slot-open position to either a first closed position or a second closed position. In the first closed position of the latch, the latch engages an archwire with sufficient force to provide active orthodontic therapy. In the second closed position, the effective labial-lingual dimension of the archwire slot is somewhat greater than the overall labial-lingual dimension of the archwire such that the bracket provides passive orthodontic therapy. Further details of dual mode orthodontic brackets are described in applicant's U.S. Pat. No. 6,071,119 and entitled "DUAL MODE SELF LIGATING ORTHODONTIC BRACKET".

In all of the embodiments described above, the latch is made of a material having sufficient inherent memory to self-return to its original shape once pressure on the latch has been relieved. As a result, the latch does not permanently deform and can be used repeatedly, even in instances where the archwire has opened the latch a number of times during treatment. Other aspects of the latches 52a–52z or other features of the appliances 30a–30z that are not described in detail are similar to corresponding aspects of the latch 52 or features of the appliance 30.

A hand instrument 110 that is especially adapted for use with some of the appliances mentioned above is illustrated in FIGS. 44–48. The hand instrument 110 is adapted to open the latch of an orthodontic appliance when desired in order to intentionally release an archwire from the archwire slot of the appliance.

Figure 44:
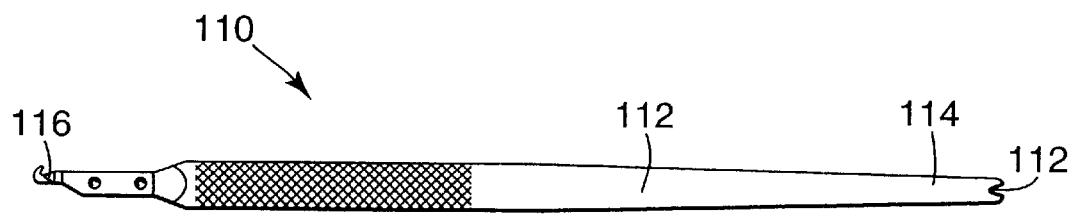
FIG. 44 is a side elevational view of a hand instrument that is particularly useful for releasing an archwire from an archwire slot of certain of the appliances described above.

As shown in FIG. 44, the hand instrument 110 includes an elongated shaft 112 with an outer end 114. The opposite end of the shaft 112 includes at least one leg for engaging an archwire and urging the archwire in a direction away from a base of the appliance. In the illustrated embodiment, the hand instrument 110 has two legs 116 having a generally "J"-shaped configuration.

Figure 45:
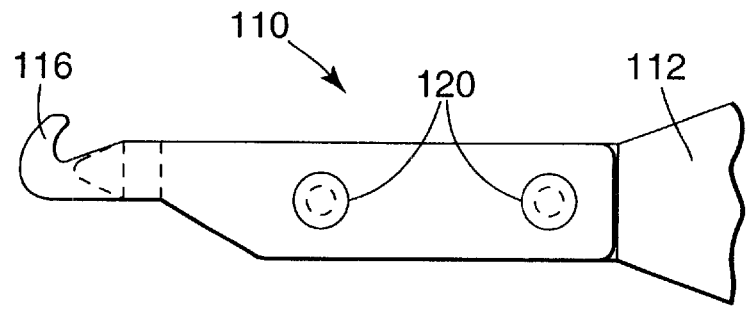
FIG. 45 is an enlarged, fragmentary side elevational view of a front portion of the hand instrument shown in FIG. 44.
Figure 46:
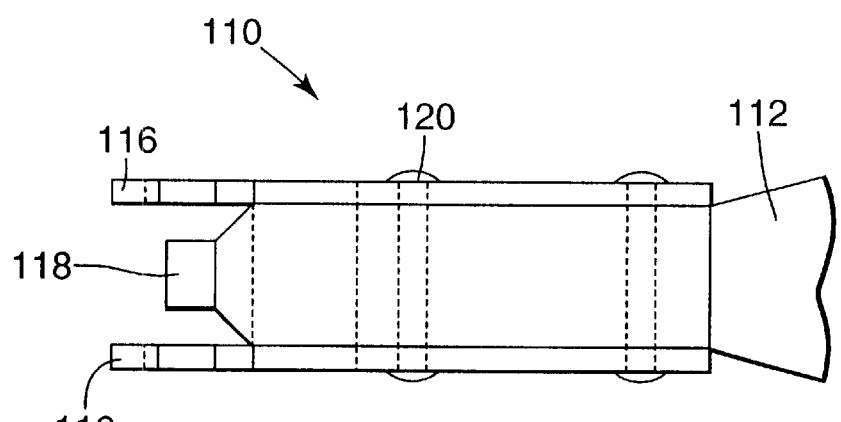
FIG. 46 is an enlarged, fragmentary elevational view taken along another side of the front portion of the hand instrument depicted in FIG. 45.

The legs 116 of the hand instrument 110 are shown in more detail in FIGS. 45 and 46. The legs 116 are spaced apart from each other and extend in parallel planes that lie on opposite sides of a central cam section 118 (FIG. 46). In this embodiment, the cam section 118 is located at a front end of the shaft 112, although other constructions are also possible.

Optionally, the legs 116 are stamped from sections of sheet metal and are connected by rivets 120 to a front portion of the shaft 112. The shaft 112 is preferably made of stainless steel.

Figure 47:
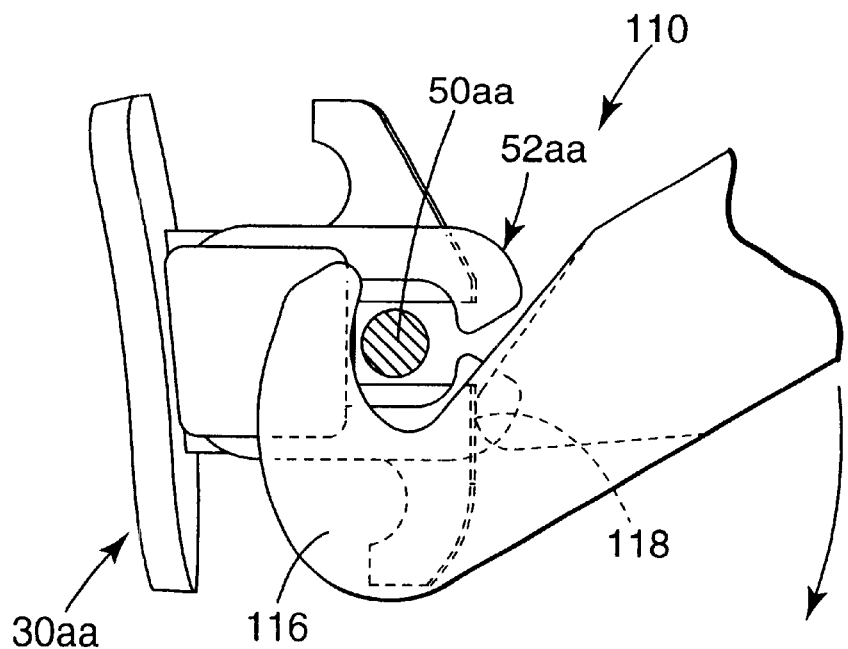
FIG. 47 is an enlarged fragmentary side elevational view of a front portion of the hand instrument illustrated in FIGS. 44–46 along with an exemplary orthodontic appliance constructed according to the invention, wherein the hand instrument is shown as it might appear after it is brought into position for release of an archwire from an archwire slot of the appliance.
Figure 48:
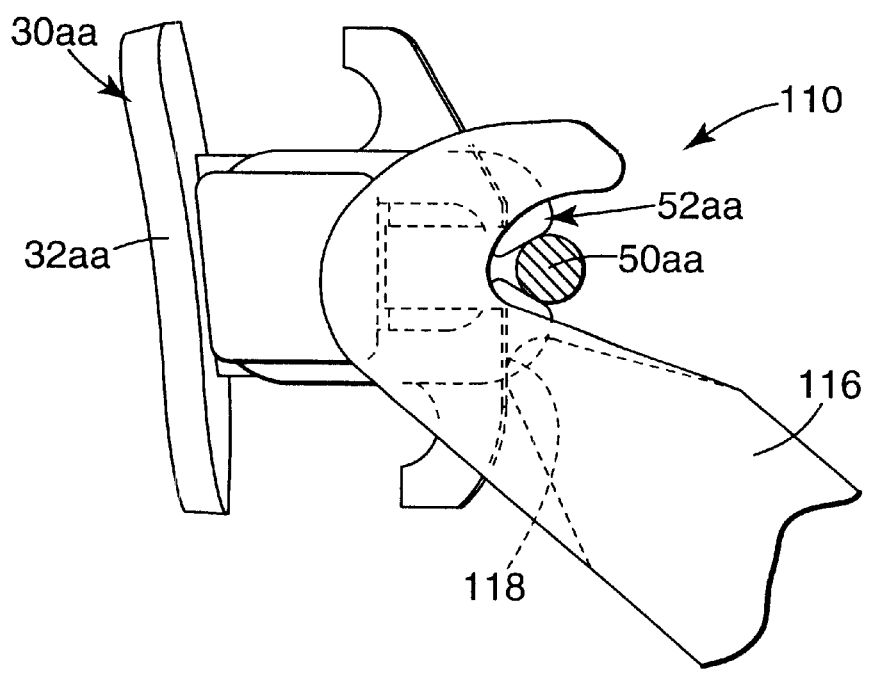
FIG. 48 is a view somewhat similar to FIG. 47 except that the hand instrument has been moved in an arc in order to release the archwire from the archwire slot.

An example of use of the hand instrument 110 is depicted in FIGS. 47 and 48. Initially, the user manipulates the hand instrument 110 to an orientation such as shown in FIG. 47 in order to bring the legs 116 in a position along a tooth-facing side of an archwire 50aa. The distance between the legs 116 is sufficient to enable an orthodontic appliance 30aa to be received within the space between the legs 116.

As the legs 116 are placed along the tooth-facing side of the archwire 50aa, the cam section 118 of the hand instrument 110 comes into contact with the appliance 30aa as shown in FIG. 47. In this embodiment, the cam section 118 engages a labial side of at least one gingival tiewing of the appliance 30aa, although other constructions are possible. For example, the cam section 118 could be arranged to contact a base 32aa of the appliance 30aa.

Next, the shaft 112 of the hand instrument 110 is rocked in a generally occlusal-gingival direction. In FIG. 47, the hand instrument 110 is rocked in a gingival direction as shown by the arrow, although an opposite orientation and direction of motion are also possible. During such rocking motion, the legs 116 urge the archwire 50aa against a latch 52aa having opposed arm portions. As the shaft 118 continues to move in the direction of the arrow, the legs 116 push the archwire 50aa against the latch 52aa with sufficient force to release the archwire 50aa from the archwire slot as shown in FIG. 48.

The hand instrument 110 is an advantage, in that the cam section 118 bears against the appliance 30aa in an area spaced from the latch 52aa as the archwire 50aa is released. Such construction helps to ensure that the appliance 30aa is not unintentionally debonded from the tooth as the archwire 50aa is pushed past the arm portions of the latch 52aa.

Optionally, the rear end 114 of the shaft 112 may be provided with a notch 122 for receiving the archwire 50aa. The notch 122 may be used if desired for placing the archwire 50aa in the archwire slot of the appliance 30x. Although movement of the archwire 50aa into the archwire slot by use of the practitioner's finger pressure directly on the archwire 50aa is efficient, there may be certain circumstances where use of the hand instrument 110 for placing the archwire 50aa in the archwire slot is desired.

Figure 49:
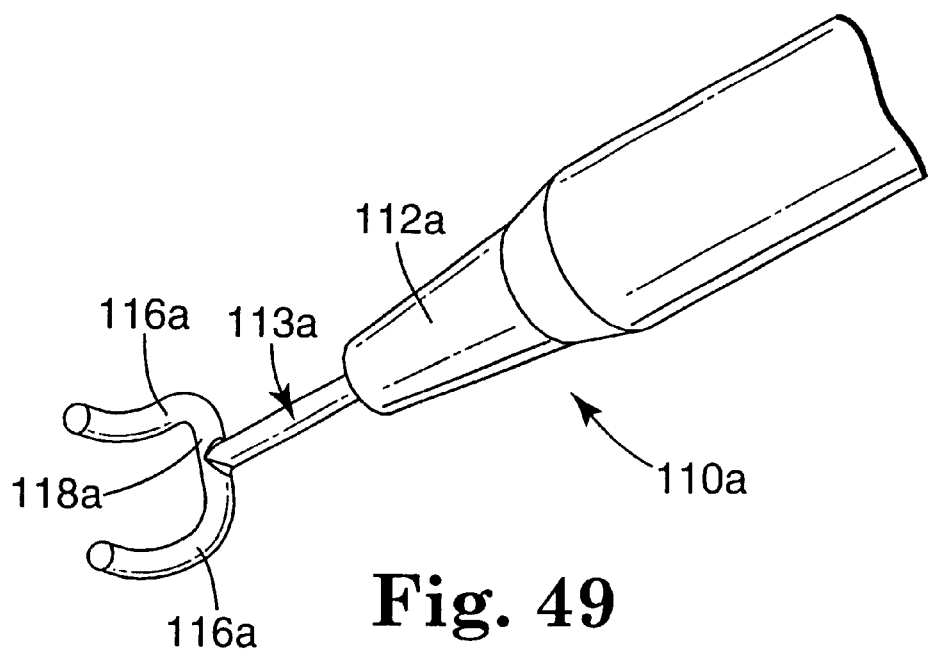
FIG. 49 is a fragmentary perspective view of a front portion of a hand instrument for releasing an archwire from an orthodontic appliance according to another embodiment of the invention.

A hand instrument 110a according to another embodiment of the invention is illustrated in FIG. 49. The hand instrument 110a includes a wire member 113a having a bifurcated front end portion. The front end portion of the wire member 113a presents two spaced apart legs 116a, each of which has a generally "L"-shaped configuration. A central section 118a interconnects the legs 116a.

In use of the hand instrument 110a to release an archwire from an archwire slot of a self-releasing orthodontic appliance, the legs 116a are positioned on a tooth-facing side or lingual side (for labial appliances) of the archwire. In this position, the legs 116a straddle opposite sides of the appliance. Next, the shaft 112a is rocked in a mesial-distal direction. For example, if the shaft 112a is rocked in a mesial direction, the leg 116a adjacent the mesial side of the appliance will bear against the base of the appliance while the opposite leg 116a urges the archwire to open the latch adjacent the distal side of the appliance. The rocking motion is continued in that direction until the archwire is released from the distal latch.

Next, the shaft 112a is rocked in an opposite direction, or in a distal direction in the example set out above. In that instance, the distal leg 116a bears against a distal side of the appliance base while the opposite leg urges the archwire against the mesial latch of the appliance. Continued movement of the shaft 112a opens the latch on the mesial side of the appliance and releases the archwire from the mesial latch. At that time, the archwire is fully released from the appliance and the hand instrument 110a can be removed from its position behind the archwire.

Figure 50:
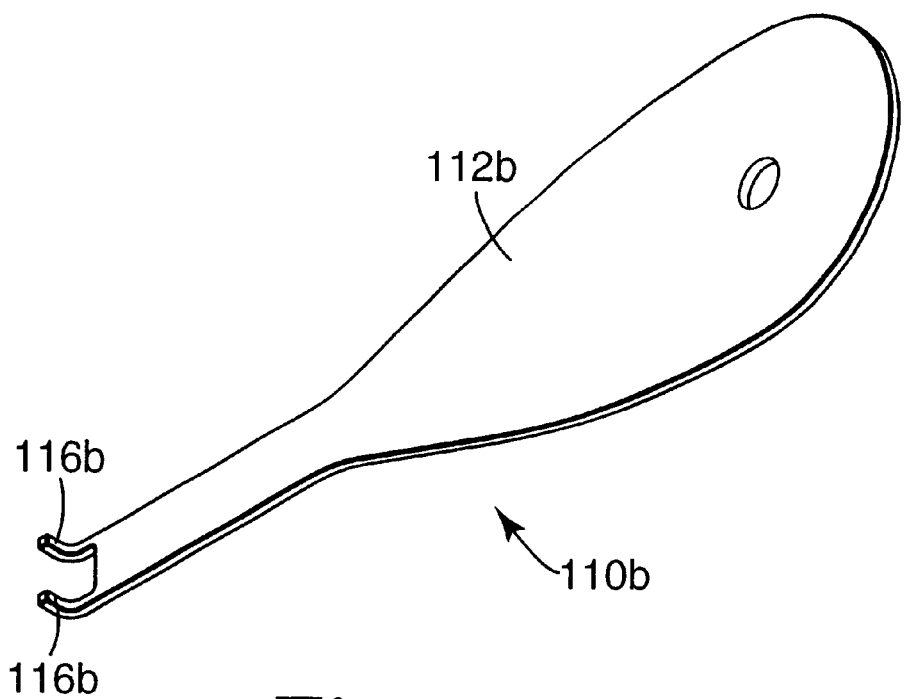
FIG. 50 is a perspective view of a hand instrument for releasing an archwire from an orthodontic appliance according to still another embodiment of the invention.

A hand instrument 110b according to another embodiment of the invention is illustrated in FIG. 50. The hand instrument 110b is somewhat similar to the hand instruments 110, 110a in that the hand instrument 110b has an elongated shaft 112b and a pair of legs 116b. However, the hand instrument 110b is an advantage, in that it is constructed from a unitary sheet of material that may be stamped and then bent to the desired configuration. For example, the hand instrument 110b may be stamped from a metallic material such as stainless steel series 400, and thus made in a relatively inexpensive manner.

Figure 51:
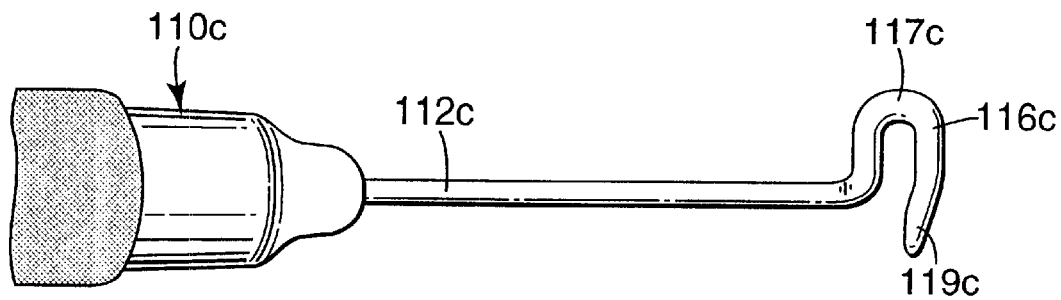
FIG. 51 is a fragmentary perspective view of a front portion of a hand instrument for releasing an orthodontic archwire from an orthodontic appliance according to still another embodiment of the invention.
Figure 52:
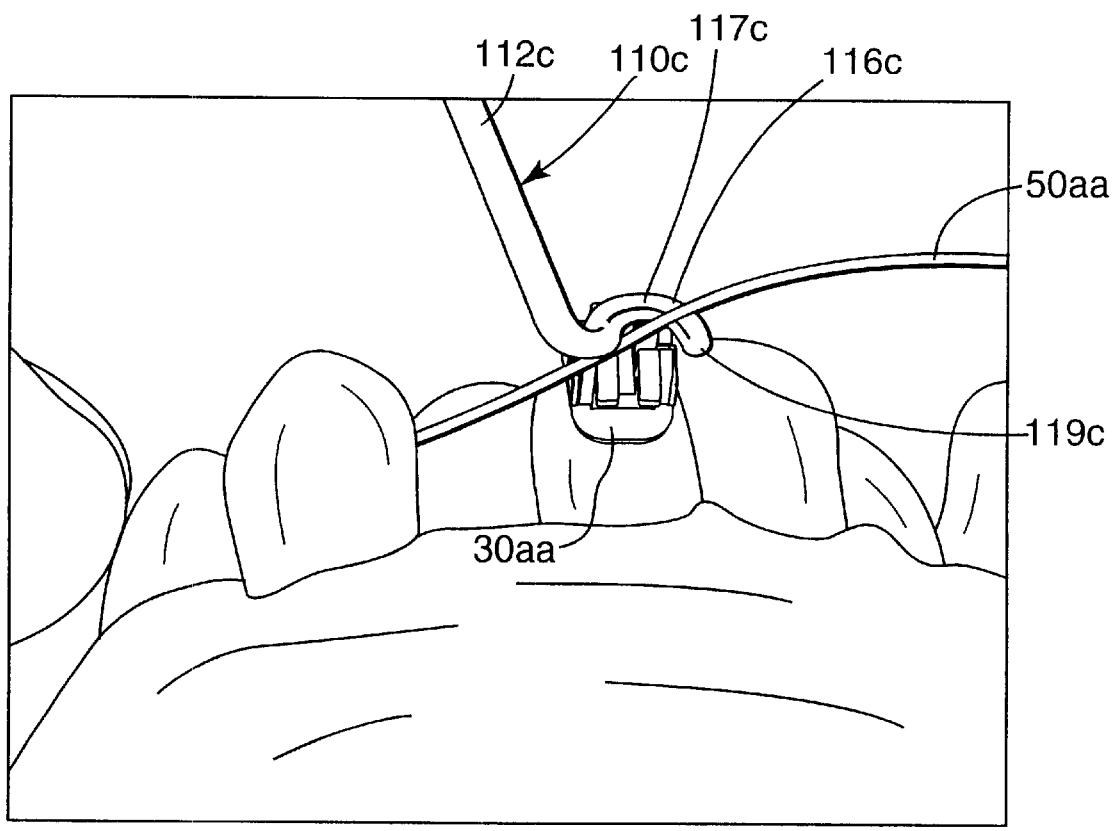
FIG. 52 is a fragmentary perspective view illustrating an example of use of the hand instrument shown in FIG. 51 during release of an archwire from an archwire slot of an orthodontic appliance.

A hand instrument 110c according to another embodiment of the invention is illustrated in FIGS. 51 and 52. The hand instrument 110c includes an elongated shaft 112c, a portion of which is shown in the drawings. The hand instrument 10c has a single leg 116c with a generally "U"-shaped section 117c and an outer, terminal end section 119c. As can be appreciated by reference to FIG. 52, the end section 119c extends at a slight acute angle relative to the outer leg of the "U"-shaped section 117c.

An example of use of the hand instrument 110c is depicted in FIG. 52. As shown, the hand instrument 110c is positioned so that the archwire 50aa extends through the "U"-shaped section 117c, preferably so that it lies at the intersection of the end section 119c and the "U"-shaped section 117c. Next, the shaft 112c is rocked in a generally mesial-distal direction and an opposite part of the "U"-shaped section bears against the appliance 30aa. As the shaft 112c continues to be pivoted in the same mesial-distal direction, the archwire 50aa is pressed against the latch in order to open the latch and release the archwire 50aa from the archwire slot.

Next, the hand instrument 110c is disengaged from the archwire 50aa and rotated approximately 180 degrees about its longitudinal axis in order to be placed in a position opposite that shown in FIG. 52. Again, the hand instrument 10c is manipulated so that the archwire extends through the middle of the "U"-shaped section 117c. As the shaft 112c is rocked in a direction opposite to the direction of motion described above, the archwire 50aa is pressed against the remaining latch of the appliance 30aa in order to open that latch and completely release the archwire 50aa from the archwire slot of the appliance 30aa.

Those skilled in the art may recognize that a number of modifications and additions are possible to the presently preferred embodiments that are described in detail above. For example, the latches as mentioned above may be utilized with a variety of other types of orthodontic appliances including single tiewing brackets, three wing brackets and the like. Alternatively, the tiewings may be omitted if desired. The latches could also be used with buccal tube appliances having an open slot, and in such appliances the tiewings are optional.

Additionally, the appliances may be made of materials other than metal, including ceramics, plastics and the like. Optionally, the archwire slots of the appliances may include an archwire slot liner or may be coated with a material to facilitate movement of the appliance along the archwire. A number of other variations are also possible. Accordingly, the invention should not be deemed limited to the specific embodiments described above, but instead only by a fair scope of the claims that follow along with their equivalents.

What is claimed is:

1. An orthodontic appliance comprising:
   a base for bonding an appliance to a tooth;
   a body extending from the base;
   an archwire slot extending across the body in a generally mesial-distal direction; and
   a latch connected to the body for releasably retaining an archwire in the archwire slot, wherein the latch releases the archwire from the archwire slot in a certain direction whenever the archwire exerts a force in the range of about 0.1 kg to about 5 kg in the same direction on the appliance.

2. An orthodontic appliance according to claim 1 wherein the latch releases the archwire from the archwire slot whenever the archwire exerts a force in the range of about 0.2 kg to about 2.5 kg in the same direction on the appliance.

3. An orthodontic appliance according to claim 1 where in the latch releases the archwire from the archwire slot whenever the archwire exerts a force in the range of about 0.2 kg to about 1.25 kg in the same direction on the appliance.

4. An orthodontic appliance according to claim 1 wherein the latch is movable to the slot-open position by pressing the archwire against the latch in a generally lingual direction.

5. An orthodontic appliance according to claim 1 wherein the latch includes at least one arm portion that is movable outwardly to release the archwire.

6. An orthodontic appliance according to claim 1 wherein the latch includes a mesial clip and a distal clip, and wherein each of the clips have an overall, generally "C"-shaped configuration.

7. An orthodontic appliance according to claim 6 wherein the body includes a mesial side and a distal side, and wherein the mesial clip is secured to the mesial side and the distal clip is secured to the distal side.

8. An orthodontic appliance according to claim 1 wherein the appliance includes a channel extending in a generally occlusal-gingival direction, and wherein the latch includes a lingual portion that is received in the channel.

9. An orthodontic appliance according to claim 8 wherein the channel extends in the body.

10. An orthodontic appliance according to claim 8 wherein the latch also includes a pair of arm portions that extend toward each other along a path located labially of the archwire slot.

11. An orthodontic appliance according to claim 8 wherein the appliance includes a pair of mesial tiewing portions and a pair of distal tiewing portions, and wherein the latch extends between the pair of mesial tiewing portions and the pair of distal tiewing portions.

12. An orthodontic appliance according to claim 1 wherein the latch includes at least two clips having an overall, generally "C"-shaped configuration, and wherein at least one clip extends further than at least one other clip in a buccolabial direction.

13. An orthodontic appliance according to claim 1 wherein the latch has an overall, generally "C"-shaped configuration with at least two independently movable side-by-side sections.

14. An orthodontic appliance according to claim 1 wherein the latch has an overall, generally "C"-shaped configuration.

15. An orthodontic appliance according to claim 14 wherein the latch has a lingual portion with a generally "W"-shaped configuration.

16. An orthodontic appliance comprising:
   a base for bonding the appliance to a tooth;
   a body extending from the base;
   an archwire slot extending across the body in a generally mesial-distal direction; and
   a latch connected to the body for releasably retaining an archwire in the archwire slot, wherein the latch releases the archwire from the archwire slot whenever the archwire exerts a force in a certain direction on the appliance that exceeds a certain minimum value, and wherein the minimum value is less than about one-half of the force required in the same direction to debond the appliance from the tooth.

17. An orthodontic appliance according to claim 16 wherein the latch is movable to a slot-open position to enable passage of the archwire into the archwire slot, and wherein the latch when in the slot-open position has a different orientation relative to the body than the orientation of the latch when the latch releases the archwire from the archwire slot.

18. An orthodontic appliance according to claim 16 wherein the latch is movable to the slot-open position by pressing the archwire against the latch in a direction generally opposite than the certain direction.

19. An orthodontic appliance according to claim 16 wherein the latch includes at least one clip have an overall, generally "C"-shaped configuration.

20. An orthodontic appliance according to claim 19 wherein the body includes a mesial side and a distal side, wherein the latch includes a mesial clip and a distal clip, and wherein the mesial clip is secured to the mesial side and the distal clip is secured to the distal side.

21. An orthodontic appliance according to claim 16 wherein the body includes a channel extending in a generally occlusal-gingival direction, and wherein the latch includes a lingual portion that is received in the channel.

22. An orthodontic appliance according to claim 21 wherein the latch also includes a pair of arm portions that extend toward each other along a path located labially of the archwire slot.

23. An orthodontic appliance according to claim 22 wherein the arm portions are movable away from each other to release the archwire.

24. An orthodontic appliance according to claim 16 wherein the appliance includes a pair of mesial tiewing portions and a pair of distal tiewing portions, and wherein the latch extends between the pair of mesial tiewing portions and the pair of distal tiewing portions.

25. An orthodontic appliance according to claim 24 wherein the latch has an overall, generally "C"-shaped configuration.

26. An orthodontic appliance according to claim 16 wherein the latch releases the archwire from the archwire slot whenever the archwire exerts a force in the range of about 0.1 kg to about 5 kg in the same direction on the appliance.

27. An orthodontic appliance according to claim 16 wherein the latch releases the archwire from the archwire slot whenever the archwire exerts a force in the range of about 0.2 kg to about 2.5 kg in the same direction on the appliance.

28. An orthodontic appliance comprising:
a base for bonding the appliance to a tooth;
a body extending from the base;
an archwire slot extending across the body in a generally mesial-distal direction and having an occlusal side, a gingival side and a lingual side;
a channel extending in a generally occlusal-gingival direction along a path located lingually of the archwire slot; and
a latch connected to the body for releasably retaining an archwire in the archwire slot, wherein the latch is movable to a slot-open position to enable passage of the archwire into the slot by pressing the archwire against the latch in a direction toward the lingual side of the archwire slot, wherein the latch includes a lingual portion that is received in the channel, and wherein the latch includes a pair of arm portions that extend toward each other along a labial side of the archwire slot.

29. An orthodontic appliance according to claim 28 wherein the appliance includes a pair of mesial tiewing portions and a pair of distal tiewing portions, and wherein the latch extends between the pair of mesial tiewing portions and the pair of distal tiewing portions.

30. An orthodontic appliance according to claim 29 wherein the archwire slot includes a mesial archwire slot relief area and a distal archwire slot relief area.

31. An orthodontic appliance according to claim 29 wherein the body is comprised of a ceramic material and wherein the archwire slot is comprised of a metallic material.

32. An orthodontic appliance according to claim 29 wherein the latch comprises at least one clip having a generally overall "C"-shaped configuration.

33. An orthodontic appliance according to claim 32 wherein the latch comprises two or more side-by-side clips each having a generally overall "C"-shaped configuration.

34. An orthodontic appliance according to claim 28 wherein the channel is spaced from the archwire slot.

35. An orthodontic appliance according to claim 34 wherein the body includes a section that extends between the archwire slot and the channel.

36. An orthodontic appliance according to claim 28 wherein the latch comprises at least one clip having an overall, generally "C"-shaped configuration.

37. An orthodontic appliance according to claim 36 wherein the latch is comprised of a shape-memory alloy material.

38. An orthodontic appliance according to claim 28 wherein the latch has an overall, generally "C"-shaped configuration with a lingual portion, an occlusal portion and a gingival portion, and wherein the body includes a first section that extends between the lingual portion of the latch and the archwire slot, a second section that extends between the occlusal portion of the latch and the archwire slot, and a third section that extends between the gingival portion of the latch and the archwire slot.

39. An orthodontic appliance according to claim 28 wherein the latch includes at least one arm portion that is movable outwardly to release the archwire.

40. An orthodontic appliance according to claim 28 wherein the latch releases the archwire whenever the archwire exerts a force in a certain direction on the appliance that exceeds a certain minimum value, and wherein the minimum value is less than about one-half of the force required in the same direction to debond the appliance from the tooth.

41. An orthodontic appliance according to claim 28 wherein the latch releases the archwire from the archwire slot whenever the archwire exerts a force in the range of about 0.1 kg to about 5 kg in the same direction on the appliance.

42. An orthodontic appliance according to claim 28 wherein the latch releases the archwire from the archwire slot whenever the archwire exerts a force in the range of about 0.2 kg to about 2.5 kg in the same direction on the appliance.

43. A method of releasing an archwire from an archwire slot of an orthodontic appliance comprising:
placing at least one leg of a hand instrument along a tooth-facing side of the archwire;
manipulating the hand instrument in order to urge the archwire in a direction toward a latch of the appliance; and
pressing the archwire against the latch with sufficient force to open the latch and release the archwire from the archwire slot, wherein the act of manipulating the hand instrument includes the act of bearing against the appliance with the hand instrument in an area spaced from the latch as the archwire is pressed against the latch.

44. The method of claim 43 wherein the act of manipulating the hand instrument in order to urge the archwire in a direction toward a latch of the appliance includes the act of pivoting the hand instrument.

45. The method of claim 44 wherein the act of pivoting the hand instrument includes the act of placing a section of the hand instrument against the appliance while the hand instrument is pivoted.

46. The method of claim 45 wherein the act of placing a section of the hand instrument against the appliance includes the act of placing a section of the hand instrument against a tiewing of the appliance.

47. The method of claim 45 wherein the act of placing a section of the hand instrument against the appliance includes the act of placing a section of the hand instrument against a base of the appliance.

48. The method of claim 44 wherein the act of pivoting the hand instrument includes the act of rocking an elongated shaft of the hand instrument in a generally occlusal-gingival direction.

49. The method of claim 44 wherein the act of pivoting the hand instrument includes the act of placing a section of the hand instrument against a tooth while the hand instrument is pivoted.

50. The method of claim 44 wherein the act of pivoting the hand instrument includes the act of rocking an elongated shaft of the hand instrument in a generally mesial-distal direction.

51. The method of claim 43 wherein the act of manipulating the hand instrument includes the act of moving the hand instrument in order to engage the archwire adjacent a mesial side of the appliance and also adjacent a distal side of the appliance.

52. The method of claim 51 wherein the act of moving the hand instrument includes the act of engaging the archwire adjacent a mesial side of the appliance simultaneously with the act of engaging the archwire adjacent a distal side of the appliance.

* * * * *

UNITED STATES PATENT AND TRADEMARK OFFICE
CERTIFICATE OF CORRECTION

PATENT NO. : 6,582,226 B2
DATED : June 24, 2003
INVENTOR(S) : Jordan, Russell A.

It is certified that error appears in the above-identified patent and that said Letters Patent is hereby corrected as shown below:

Column 10,
Line 6, "40a" should read -- 40 a --.

Column 12,
Line 32, "50" should read -- 40 --.
Line 35, "archwire 40" should read -- archwire 50 --.

Column 13,
Lines 20 and 22, "discreet" should read -- discrete --.
Line 62, "discreet" should read -- discrete --.

Column 15,
Line 54, "52e" should read -- 54e --.

Column 16,
Line 5, "discreet" should read -- discrete --.
Line 21, "5 if" should read -- 51f --.
Line 25, "is" should read -- in --.
Line 28, "54f" should read -- 51f --.
Line 30, "40f" should read -- 41f --.

Column 17,
Line 48, "69h" should read -- 68h --.

Column 19,
Line 37, "78L" should read -- 74L --.

Column 22,
Line 11, "32p" should read -- 52p --.
Line 63, "92g" should read -- 96g --.

Column 23,
Line 9, "92g" should read -- 96g --.
Line 28, "80r" should read -- 52r --.

UNITED STATES PATENT AND TRADEMARK OFFICE
CERTIFICATE OF CORRECTION

PATENT NO.   : 6,582,226 B2
DATED        : June 24, 2003
INVENTOR(S)  : Jordan, Russell A.

It is certified that error appears in the above-identified patent and that said Letters Patent is hereby corrected as shown below:

<u>Column 27,</u>
Line 6, "75z" should read -- 68z, 70z --.

<u>Column 28,</u>
Line 19, "118" should read -- 112 --.
Line 34, "30x" should read -- 30aa --.

<u>Column 29,</u>
Lines 17 and 38, "10c" should read -- 110c --.

Signed and Sealed this

Twenty-third Day of December, 2003

JAMES E. ROGAN
*Director of the United States Patent and Trademark Office*